United States Patent
Patterson et al.

(10) Patent No.: US 9,655,745 B2
(45) Date of Patent: May 23, 2017

(54) METHODS FOR MANUFACTURING IMPLANTS HAVING INTEGRATION SURFACES

(71) Applicant: Titan Spine, LLC, Mequon, WI (US)

(72) Inventors: Chad J. Patterson, Port Washington, WI (US); Mark E. Berg, Fort Wayne, IN (US); Peter F. Ullrich, Jr., Neenah, WI (US)

(73) Assignee: Titan Spine, LLC, Mequon, WI (US)

( * ) Notice: Subject to any disclaimer, the term of this patent is extended or adjusted under 35 U.S.C. 154(b) by 0 days.

(21) Appl. No.: 14/934,675

(22) Filed: Nov. 6, 2015

(65) Prior Publication Data

US 2016/0058574 A1 Mar. 3, 2016

Related U.S. Application Data

(63) Continuation of application No. 13/566,384, filed on Aug. 3, 2012, now abandoned, which is a
(Continued)

(51) Int. Cl.
*A61F 2/44* (2006.01)
*B23K 26/362* (2014.01)
(Continued)

(52) U.S. Cl.
CPC .......... *A61F 2/4455* (2013.01); *B23K 26/362* (2013.01); *B29C 59/16* (2013.01);
(Continued)

(58) Field of Classification Search
CPC .. A61F 2/44; A61F 2/4455; A61F 2002/4475; A61F 2002/30838;
(Continued)

(56) References Cited

U.S. PATENT DOCUMENTS

| 4,314,876 A | 2/1982 | Kremer et al. |
| 4,904,261 A | 2/1990 | Dove et al. |

(Continued)

FOREIGN PATENT DOCUMENTS

| EP | 0599419 | 6/1994 |
| EP | 0916323 | 5/1999 |

(Continued)

OTHER PUBLICATIONS

Astra Tech Dental, "Nanolevel topographic modifications on the OsseoSpeed surface", http://shop.dentsplyimplants.us, Mar. 8, 2001.
(Continued)

*Primary Examiner* — Eduardo C Robert
*Assistant Examiner* — Julianna N Harvey
(74) *Attorney, Agent, or Firm* — Stradley Ronon Stevens & Young, LLP

(57) ABSTRACT

A method of producing an interbody spinal implant. The method includes the steps of obtaining a blank having a top surface, bottom surface, opposing lateral sides, and opposing anterior and posterior portions, and applying a subtractive process (e.g., masked acid etching) to the top surface, the bottom surface, or both surfaces of the blank to form a roughened surface topography. Subsequently, the blank is machined to form the interbody spinal implant, which includes a body having a top surface, a bottom surface, opposing lateral sides, opposing anterior and posterior portions, a substantially hollow center, and a single vertical aperture where the top surface, the bottom surface, or both surfaces of the interbody spinal implant have the roughened surface topography produced by the subtractive process. This simplified method produces more accurate and repeatable implants with fewer process steps and defects, reducing process time and costs.

14 Claims, 19 Drawing Sheets

Related U.S. Application Data continuation-in-part of application No. 12/151,198, filed on May 5, 2008, now Pat. No. 8,262,737, which is a continuation-in-part of application No. 11/123,359, filed on May 6, 2005, now Pat. No. 7,662,186.

(51) Int. Cl.

| | | |
|---|---|---|
| *B29C 59/16* | (2006.01) | |
| *C23C 14/34* | (2006.01) | |
| *A61F 2/30* | (2006.01) | |
| *A61F 2/28* | (2006.01) | |
| *A61F 2/46* | (2006.01) | |
| *B29K 101/00* | (2006.01) | |

(52) U.S. Cl.
CPC .......... *C23C 14/34* (2013.01); *A61F 2/30965* (2013.01); *A61F 2/4465* (2013.01); *A61F 2/4611* (2013.01); *A61F 2002/2817* (2013.01); *A61F 2002/2835* (2013.01); *A61F 2002/305* (2013.01); *A61F 2002/30013* (2013.01); *A61F 2002/30014* (2013.01); *A61F 2002/3084* (2013.01); *A61F 2002/3093* (2013.01); *A61F 2002/3097* (2013.01); *A61F 2002/30133* (2013.01); *A61F 2002/30273* (2013.01); *A61F 2002/30321* (2013.01); *A61F 2002/30405* (2013.01); *A61F 2002/30433* (2013.01); *A61F 2002/30441* (2013.01); *A61F 2002/30454* (2013.01); *A61F 2002/30469* (2013.01); *A61F 2002/30472* (2013.01); *A61F 2002/30481* (2013.01); *A61F 2002/30507* (2013.01); *A61F 2002/30604* (2013.01); *A61F 2002/30769* (2013.01); *A61F 2002/30772* (2013.01); *A61F 2002/30774* (2013.01); *A61F 2002/30779* (2013.01); *A61F 2002/30785* (2013.01); *A61F 2002/30787* (2013.01); *A61F 2002/30789* (2013.01); *A61F 2002/30836* (2013.01); *A61F 2002/30838* (2013.01); *A61F 2002/30892* (2013.01); *A61F 2002/30906* (2013.01); *A61F 2002/30925* (2013.01); *A61F 2002/30927* (2013.01); *A61F 2002/30973* (2013.01); *A61F 2002/30985* (2013.01); *A61F 2002/448* (2013.01); *A61F 2002/4475* (2013.01); *A61F 2002/4629* (2013.01); *A61F 2220/0025* (2013.01); *A61F 2230/0015* (2013.01); *A61F 2240/00* (2013.01); *A61F 2250/0018* (2013.01); *A61F 2310/00017* (2013.01); *A61F 2310/00023* (2013.01); *A61F 2310/00047* (2013.01); *A61F 2310/00053* (2013.01); *A61F 2310/00131* (2013.01); *A61F 2310/00407* (2013.01); *B29K 2101/00* (2013.01); *B29K 2995/0056* (2013.01); *Y10T 29/49995* (2015.01); *Y10T 82/10* (2015.01); *Y10T 408/03* (2015.01)

(58) Field of Classification Search
CPC .... A61F 2002/3084; A61F 2002/30892; A61F 2002/30906; A61F 2002/3025; Y10T 29/49888; Y10T 29/49995; Y10T 29/49996
See application file for complete search history.

(56) References Cited

U.S. PATENT DOCUMENTS

| | | | |
|---|---|---|---|
| 5,015,247 A | 5/1991 | Michelson | |
| 5,071,437 A | 12/1991 | Steffee | |
| 5,258,098 A * | 11/1993 | Wagner | A61F 2/30767 216/41 |
| 5,306,309 A | 4/1994 | Wagner et al. | |
| 5,425,772 A | 6/1995 | Brantigan | |
| 5,443,514 A | 8/1995 | Steffee | |
| 5,456,723 A | 10/1995 | Steinemann et al. | |
| 5,507,815 A | 4/1996 | Wagner et al. | |
| 5,571,188 A | 11/1996 | Ellingsen et al. | |
| 5,603,338 A | 2/1997 | Beaty | |
| 5,609,635 A | 3/1997 | Michelson | |
| 5,702,449 A | 12/1997 | McKay | |
| 5,755,798 A | 5/1998 | Papavero et al. | |
| 5,766,252 A * | 6/1998 | Henry | A61F 2/4455 606/247 |
| 5,776,199 A | 7/1998 | Michelson | |
| 5,860,973 A | 1/1999 | Michelson | |
| 5,863,201 A | 1/1999 | Lazzara et al. | |
| 5,865,845 A | 2/1999 | Thalgott | |
| 5,876,453 A | 3/1999 | Beaty | |
| 5,885,079 A | 3/1999 | Niznick | |
| 5,888,224 A * | 3/1999 | Beckers | A61F 2/4455 623/17.16 |
| 5,922,029 A | 7/1999 | Wagner et al. | |
| 5,968,098 A | 10/1999 | Winslow | |
| 5,984,922 A | 11/1999 | McKay | |
| 6,033,582 A | 3/2000 | Lee et al. | |
| 6,039,762 A | 3/2000 | McKay | |
| 6,059,829 A | 5/2000 | Schlapfer et al. | |
| 6,080,158 A | 6/2000 | Lin | |
| 6,086,613 A | 7/2000 | Camino et al. | |
| 6,096,107 A | 8/2000 | Caracostas et al. | |
| 6,123,705 A | 9/2000 | Michelson | |
| 6,143,032 A | 11/2000 | Schafer et al. | |
| 6,168,631 B1 * | 1/2001 | Maxwell | A61B 17/562 623/17.11 |
| 6,176,882 B1 | 1/2001 | Biedermann et al. | |
| 6,183,255 B1 | 2/2001 | Oshida | |
| 6,193,757 B1 | 2/2001 | Foley et al. | |
| 6,193,762 B1 | 2/2001 | Wagner et al. | |
| 6,241,770 B1 | 6/2001 | Michelson | |
| 6,241,771 B1 | 6/2001 | Gresser et al. | |
| 6,245,108 B1 | 6/2001 | Biscup | |
| 6,296,664 B1 | 10/2001 | Middleton | |
| 6,302,914 B1 | 10/2001 | Michelson | |
| 6,342,074 B1 | 1/2002 | Simpson | |
| 6,344,057 B1 | 2/2002 | Rabbe et al. | |
| 6,350,283 B1 | 2/2002 | Michelson | |
| 6,375,681 B1 | 4/2002 | Truscott | |
| 6,387,130 B1 | 5/2002 | Stone et al. | |
| 6,395,031 B1 | 5/2002 | Foley et al. | |
| 6,423,095 B1 | 7/2002 | Van Hoeck et al. | |
| 6,432,140 B1 | 8/2002 | Lin | |
| 6,447,544 B1 | 9/2002 | Michelson | |
| 6,458,159 B1 | 10/2002 | Thalgott | |
| 6,478,823 B1 | 11/2002 | Michelson | |
| 6,482,233 B1 | 11/2002 | Aebi et al. | |
| 6,485,517 B1 | 11/2002 | Michelson | |
| 6,491,723 B1 | 12/2002 | Beaty | |
| 6,558,424 B2 | 5/2003 | Thalgott | |
| 6,569,201 B2 | 5/2003 | Moumene et al. | |
| 6,579,318 B2 | 6/2003 | Varga et al. | |
| 6,592,624 B1 | 7/2003 | Fraser et al. | |
| 6,599,322 B1 | 7/2003 | Amrich et al. | |
| 6,610,089 B1 | 8/2003 | Liu et al. | |
| 6,620,332 B2 | 9/2003 | Amrich | |
| 6,635,086 B2 | 10/2003 | Lin | |
| 6,652,765 B1 | 11/2003 | Beaty | |
| 6,676,703 B2 | 1/2004 | Biscup | |
| 6,702,855 B1 | 3/2004 | Steinemann et al. | |
| 6,719,794 B2 | 4/2004 | Gerber et al. | |
| 6,726,720 B2 | 4/2004 | Ross et al. | |
| 6,730,127 B2 | 5/2004 | Michelson | |
| 6,740,118 B2 | 5/2004 | Eisermann et al. | |
| 6,743,231 B1 | 6/2004 | Gray et al. | |
| 6,758,849 B1 | 7/2004 | Michelson | |
| 6,833,006 B2 | 12/2004 | Foley et al. | |
| 6,890,355 B2 | 5/2005 | Michelson | |
| 6,902,581 B2 | 6/2005 | Walkenhorst et al. | |
| 6,911,249 B2 | 6/2005 | Wagner et al. | |

(56) References Cited

U.S. PATENT DOCUMENTS

| | | |
|---|---|---|
| 6,923,810 B1 | 8/2005 | Michelson |
| 6,974,480 B2 | 12/2005 | Messerli et al. |
| 6,981,975 B2 | 1/2006 | Michelson |
| 7,018,418 B2 | 3/2006 | Amrich et al. |
| 7,041,137 B2 | 5/2006 | Fulton et al. |
| 7,044,972 B2 | 5/2006 | Mathys, Jr. et al. |
| 7,048,870 B1 | 5/2006 | Ellingsen et al. |
| 7,060,073 B2 | 6/2006 | Frey et al. |
| 7,066,961 B2 | 6/2006 | Michelson |
| 7,077,864 B2 | 7/2006 | Byrd, III et al. |
| 7,087,085 B2 | 8/2006 | Steinemann et al. |
| 7,112,224 B2 | 9/2006 | Lie et al. |
| 7,128,760 B2 | 10/2006 | Michelson |
| 7,137,997 B2 | 11/2006 | Paul |
| 7,144,428 B2 | 12/2006 | Anitua |
| 7,166,129 B2 | 1/2007 | Michelson |
| 7,169,183 B2 | 1/2007 | Liu et al. |
| D539,934 S | 4/2007 | Blain |
| 7,201,775 B2 | 4/2007 | Gorensek et al. |
| D541,940 S | 5/2007 | Blain |
| 7,220,280 B2 | 5/2007 | Kast et al. |
| 7,223,289 B2 | 5/2007 | Trieu et al. |
| 7,226,480 B2 | 6/2007 | Thalgott |
| 7,238,186 B2 | 7/2007 | Zdeblick et al. |
| 7,244,275 B2 | 7/2007 | Michelson |
| 7,250,060 B2 | 7/2007 | Trieu |
| 7,255,698 B2 | 8/2007 | Michelson |
| 7,288,093 B2 | 10/2007 | Michelson |
| 7,311,734 B2 | 12/2007 | Van Hoeck et al. |
| D564,095 S | 3/2008 | Blain |
| 7,347,873 B2 | 3/2008 | Paul et al. |
| D566,276 S | 4/2008 | Blain |
| 7,368,065 B2 | 5/2008 | Yang et al. |
| 7,410,501 B2 | 8/2008 | Michelson |
| 7,501,073 B2 | 3/2009 | Wen et al. |
| 7,503,933 B2 | 3/2009 | Michelson |
| 7,517,363 B2 | 4/2009 | Rogers et al. |
| D599,019 S | 8/2009 | Pimenta et al. |
| 7,569,074 B2 | 8/2009 | Eisermann et al. |
| 7,608,107 B2 | 10/2009 | Michelson |
| 7,615,078 B2 | 11/2009 | White et al. |
| 7,655,042 B2 | 2/2010 | Foley et al. |
| 7,662,186 B2 | 2/2010 | Bagga et al. |
| 7,662,190 B2 | 2/2010 | Steinemann et al. |
| 7,744,612 B2 | 6/2010 | Blain |
| 7,846,183 B2 | 12/2010 | Blain |
| 7,901,462 B2 | 3/2011 | Yang et al. |
| 7,998,172 B2 | 8/2011 | Blain |
| 8,062,304 B2 | 11/2011 | Blain et al. |
| 8,100,955 B2 | 1/2012 | Blain et al. |
| 8,142,355 B2 | 3/2012 | Blain et al. |
| 8,172,854 B2 | 5/2012 | Blain et al. |
| 8,262,737 B2 | 9/2012 | Bagga et al. |
| 2001/0001315 A1 | 5/2001 | Bates et al. |
| 2001/0014826 A1 | 8/2001 | Biedermann et al. |
| 2001/0016777 A1 | 8/2001 | Biscup |
| 2001/0039454 A1 | 11/2001 | Ricci et al. |
| 2001/0047208 A1 | 11/2001 | Michelson |
| 2002/0049497 A1 | 4/2002 | Mason |
| 2002/0087212 A1 | 7/2002 | James et al. |
| 2002/0099443 A1 | 7/2002 | Messerli et al. |
| 2002/0128716 A1 | 9/2002 | Cohen et al. |
| 2002/0138142 A1 | 9/2002 | Castro et al. |
| 2002/0138143 A1* | 9/2002 | Grooms ............... A61F 2/4455 623/17.11 |
| 2002/0161443 A1 | 10/2002 | Michelson |
| 2002/0173854 A1 | 11/2002 | Amrich |
| 2002/0188294 A1 | 12/2002 | Couture et al. |
| 2003/0014116 A1 | 1/2003 | Ralph et al. |
| 2003/0031984 A1* | 2/2003 | Rusin ................... A61K 6/0005 433/215 |
| 2003/0065401 A1* | 4/2003 | Amrich ............. A61B 17/8085 623/23.55 |
| 2003/0083668 A1 | 5/2003 | Rogers et al. |
| 2003/0105527 A1 | 6/2003 | Bresina |
| 2003/0109928 A1 | 6/2003 | Pasquet et al. |
| 2003/0125739 A1 | 7/2003 | Bagga et al. |
| 2003/0153975 A1 | 8/2003 | Byrd, III et al. |
| 2003/0176925 A1 | 9/2003 | Paponneau |
| 2003/0181980 A1 | 9/2003 | Berry et al. |
| 2003/0181981 A1 | 9/2003 | Lemaire |
| 2003/0187506 A1 | 10/2003 | Ross et al. |
| 2003/0191531 A1 | 10/2003 | Berry et al. |
| 2004/0117020 A1 | 6/2004 | Frey et al. |
| 2004/0127993 A1 | 7/2004 | Kast et al. |
| 2004/0153154 A1 | 8/2004 | Dinkelacker |
| 2004/0153160 A1 | 8/2004 | Carrasco |
| 2004/0162616 A1 | 8/2004 | Simonton et al. |
| 2004/0167632 A1 | 8/2004 | Wen et al. |
| 2004/0210309 A1 | 10/2004 | Denzer et al. |
| 2004/0230306 A1 | 11/2004 | Hoeck et al. |
| 2004/0265780 A1 | 12/2004 | Robb et al. |
| 2004/0267367 A1 | 12/2004 | O'Neil |
| 2005/0021150 A1 | 1/2005 | Michelson |
| 2005/0027360 A1 | 2/2005 | Webb et al. |
| 2005/0038512 A1 | 2/2005 | Michelson |
| 2005/0060034 A1 | 3/2005 | Berry et al. |
| 2005/0075734 A1 | 4/2005 | Fulton et al. |
| 2005/0085913 A1 | 4/2005 | Fraser et al. |
| 2005/0131416 A1 | 6/2005 | Jansen et al. |
| 2005/0147942 A1 | 7/2005 | Hall |
| 2005/0159814 A1 | 7/2005 | Karahalios |
| 2005/0221258 A1* | 10/2005 | Hall ................... A61C 8/0012 433/173 |
| 2005/0251257 A1 | 11/2005 | Mitchell et al. |
| 2006/0041313 A1 | 2/2006 | Allard et al. |
| 2006/0093646 A1 | 5/2006 | Cima et al. |
| 2006/0100705 A1 | 5/2006 | Puno et al. |
| 2006/0149372 A1 | 7/2006 | Paxson et al. |
| 2006/0149376 A1 | 7/2006 | Shimp et al. |
| 2006/0167549 A1 | 7/2006 | Mathys, Jr. et al. |
| 2006/0190079 A1 | 8/2006 | Istephanous et al. |
| 2006/0219661 A1 | 10/2006 | Towse et al. |
| 2006/0229715 A1* | 10/2006 | Istephanous .......... A61F 2/0077 623/1.46 |
| 2006/0265065 A1 | 11/2006 | Bagga et al. |
| 2006/0293748 A1 | 12/2006 | Alexander et al. |
| 2007/0010885 A1 | 1/2007 | Liu et al. |
| 2007/0093898 A1 | 4/2007 | Schwab et al. |
| 2007/0118220 A1 | 5/2007 | Liu et al. |
| 2007/0118223 A1 | 5/2007 | Allard et al. |
| 2007/0233247 A1 | 10/2007 | Schwab |
| 2007/0233248 A1 | 10/2007 | Schwab et al. |
| 2007/0260320 A1 | 11/2007 | Peterman et al. |
| 2007/0270956 A1 | 11/2007 | Heinz |
| 2007/0282441 A1 | 12/2007 | Stream et al. |
| 2007/0288028 A1 | 12/2007 | Gorensek et al. |
| 2007/0293949 A1 | 12/2007 | Salerni et al. |
| 2008/0014243 A1 | 1/2008 | Ellingsen et al. |
| 2008/0071380 A1 | 3/2008 | Sweeney |
| 2008/0077171 A1 | 3/2008 | Blain et al. |
| 2008/0195209 A1 | 8/2008 | Garcia et al. |
| 2008/0221689 A1 | 9/2008 | Chaput et al. |
| 2008/0262623 A1* | 10/2008 | Bagga .................... A61F 2/442 623/17.16 |
| 2008/0269764 A1 | 10/2008 | Blain et al. |
| 2008/0269806 A1 | 10/2008 | Zhang et al. |
| 2009/0005784 A1 | 1/2009 | Blain et al. |
| 2009/0024132 A1 | 1/2009 | Blain et al. |
| 2009/0082819 A1 | 3/2009 | Blain et al. |
| 2009/0088800 A1 | 4/2009 | Blain et al. |
| 2009/0088853 A1 | 4/2009 | Ogilvie et al. |
| 2009/0132048 A1 | 5/2009 | Denzer |
| 2009/0182432 A1 | 7/2009 | Zdeblick et al. |
| 2009/0187247 A1 | 7/2009 | Metcalf, Jr. et al. |
| 2009/0204152 A1 | 8/2009 | Blain |
| 2009/0234362 A1 | 9/2009 | Blain et al. |
| 2009/0264928 A1 | 10/2009 | Blain |
| 2009/0276049 A1 | 11/2009 | Weiland |
| 2009/0312837 A1 | 12/2009 | Eisermann et al. |
| 2009/0312842 A1 | 12/2009 | Bursac et al. |
| 2010/0121385 A1 | 5/2010 | Blain et al. |
| 2010/0173264 A1 | 7/2010 | Fredriksson et al. |
| 2010/0204798 A1 | 8/2010 | Gerbec et al. |

(56) References Cited

U.S. PATENT DOCUMENTS

| | | |
|---|---|---|
| 2010/0218854 A1 | 9/2010 | Garcia Saban et al. |
| 2010/0228288 A1 | 9/2010 | Blain |
| 2010/0249937 A1 | 9/2010 | Blain et al. |
| 2010/0274286 A1 | 10/2010 | Blain et al. |
| 2011/0040301 A1 | 2/2011 | Blain et al. |
| 2011/0082503 A1 | 4/2011 | Blain |
| 2011/0224796 A1 | 9/2011 | Weiland et al. |
| 2011/0230970 A1 | 9/2011 | Lynn et al. |
| 2011/0233169 A1 | 9/2011 | Mayfield et al. |
| 2012/0009341 A1 | 1/2012 | Noh et al. |
| 2012/0046695 A9 | 2/2012 | Blain |
| 2012/0123424 A1 | 5/2012 | Blain et al. |
| 2012/0123548 A1 | 5/2012 | Lynn et al. |
| 2012/0136443 A1 | 5/2012 | Wenzel |
| 2012/0149991 A1 | 6/2012 | Blain et al. |
| 2012/0158056 A1 | 6/2012 | Blain |
| 2012/0172991 A1 | 7/2012 | Bertele et al. |

FOREIGN PATENT DOCUMENTS

| | | |
|---|---|---|
| EP | 1449544 | 8/2004 |
| EP | 2386274 | 11/2011 |
| EP | 2386274 A1 | 11/2011 |
| JP | 2001170092 | 6/2001 |
| JP | 08010276 | 11/2011 |
| WO | 9706753 | 2/1997 |
| WO | 98/01091 | 1/1998 |
| WO | 0128469 | 4/2001 |
| WO | 0170144 | 9/2001 |
| WO | 0195838 | 12/2001 |
| WO | 2004041131 | 5/2004 |
| WO | 2006081843 | 8/2006 |
| WO | 2006119088 | 9/2006 |
| WO | 2006116306 | 11/2006 |
| WO | 2006121795 | 11/2006 |
| WO | 2007089905 | 8/2007 |
| WO | 2008103843 | 8/2008 |
| WO | 2009006225 | 1/2009 |
| WO | 2009029458 | 3/2009 |
| WO | 2009129262 | 10/2009 |
| WO | 2009140544 | 11/2009 |

OTHER PUBLICATIONS

Astra Tech Dental, "OsseoSpeed—more bone more rapidly", http://shop.dentsplyimplants.us, May 2011.

Guo, et al., "The effect of hydrofluoric acid treatment of TiO2 grit blasted titanium implants on adherent osteoblast gene expression in vitro and in vivo", Biomaterials 28 (Sep. 14, 2007) 5418-5425.

He, et al., "Mechanical and Histomorphometric Evaluations of Rough Titanium Implants Treated with Hydrofluoric Acid/Nitric Acid Solution in Rabbit Tibia", Int. J. Oral Maxillofac. Implants, Nov. 1, 2011; 26:115-122.

Isa, et al., "Effects of Fluoride-Modified Titanium Surfaces on Osteoblast Proliferation and Gene Expression", Int. J. Oral Maxillofac. Implants 2006; 21:203-211.

Lamolle, et al., "The effect of hydrofluoric acid treatment of titanium surface on nanostructural and chemical changes and the growith of MC3T3-E1 cells", Biomaterials 30 (Nov. 20, 2008) 736-742.

Meirelles, et al., "The Effect of Chemical and Nanotopographical Modifications on the Early Stages of Osseointegration", Int. J. Oral Maxillofac. Implants 2008; 23:641-647.

Supplementary Partial European Search Report issued Sep. 27, 2011.

Supplementary Partial European Search Report issued Aug. 19, 2011.

Variola, et al., "Nanoscale surface modifications of medically relevant metals: state-of-the art and prespectives", Nanoscale, 2011, 3, 335-353.

Wennerberg, et al., "Spontaneously formed nanostructures on titanium surfaces", Clin. Oral Impl. Res., 2012, 1-7.

* cited by examiner

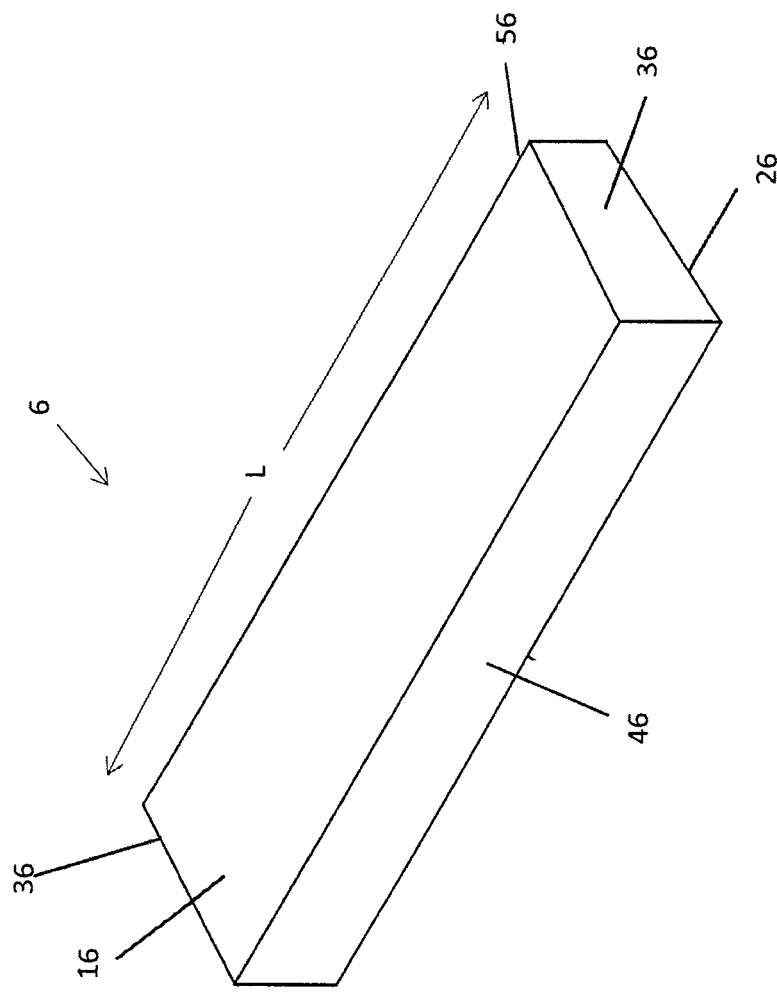
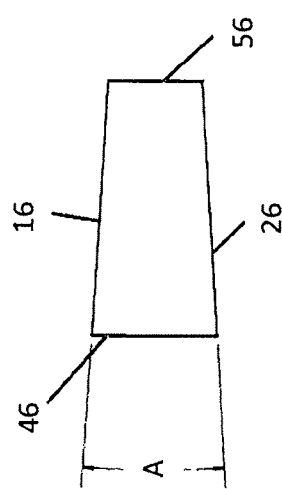

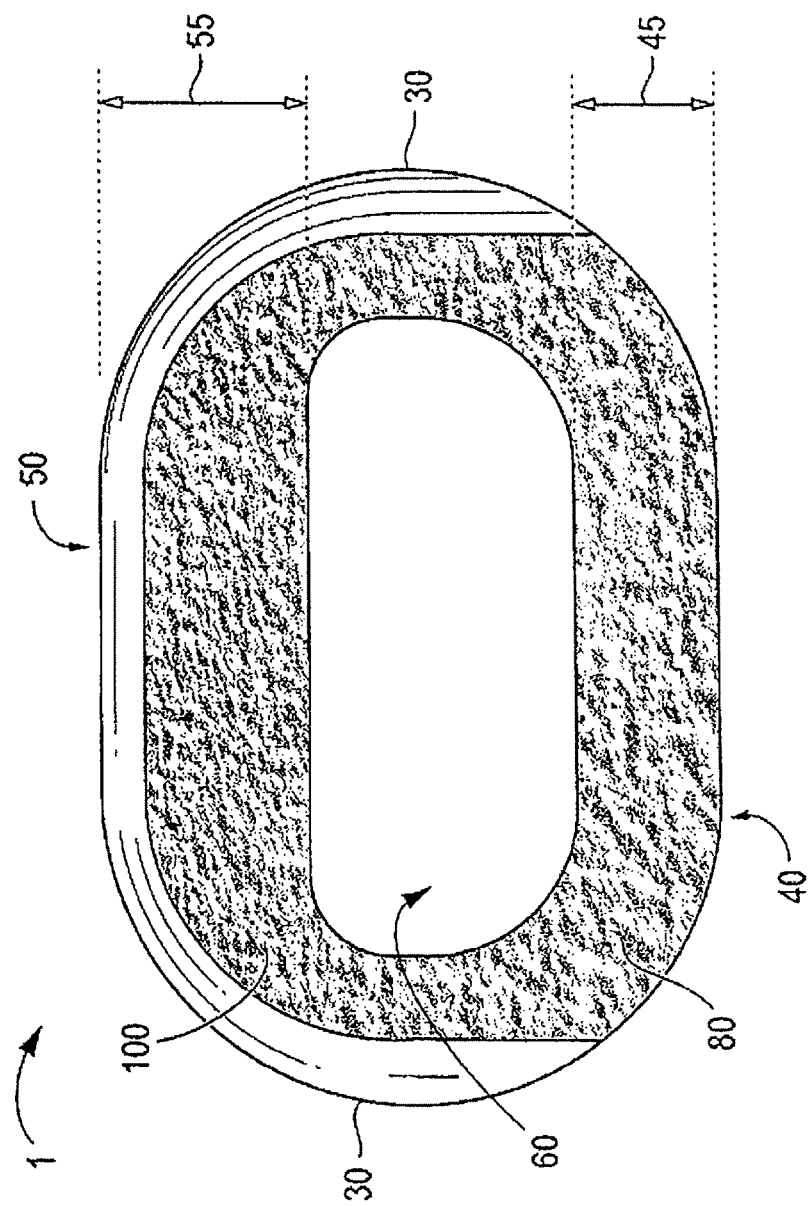

Ra = Average(1, 4, 6, 8, 5, 2, 1, 4, 1, 2, 1, 4, 7, 4, 1, 2, 5, 8, 2, 1, 4, 1, 1)

Ra = 3.26

Rpm = average(Rp1, Rp2, Rp3, ...)
Rvm = average(Rv1, Rv2, Rv3, ...)
RzDIN = Rtm = average(Rt1, Rt2, Rt3, ...)

Sm = average($S_1, S_2, S_3, ...$)

METHODS FOR MANUFACTURING IMPLANTS HAVING INTEGRATION SURFACES

CROSS REFERENCE TO RELATED APPLICATIONS

This application is a continuation of U.S. patent application Ser. No. 13/566,384, filed on Aug. 3, 2012, which is a continuation-in-part of U.S. patent application Ser. No. 12/151,198, filed on May 5, 2008, and issued as U.S. Pat. No. 8,262,737, which is a continuation-in-part of U.S. patent application Ser. No. 11/123,359, filed on May 6, 2005, and issued as U.S. Pat. No. 7,662,186. The contents of these prior applications are incorporated by reference into this document, in their entirety and for all purposes.

TECHNICAL FIELD

The present invention relates generally to improved methods of making interbody spinal implants and, more particularly, to an optimized sequence of process steps necessary to form spinal implants having integration surfaces of better quality with reduced process time and costs.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, may develop deformities such as tears or cracks, or may simply lose structural integrity (e.g., the discs may bulge or flatten). Impaired discs can affect the anatomical functions of the vertebrae, due to the resultant lack of proper biomechanical support, and are often associated with chronic back pain.

Several surgical techniques have been developed to address spinal defects, such as disc degeneration and deformity. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

Spinal fusion procedures can be achieved using a posterior or an anterior approach, for example. Anterior interbody fusion procedures generally have the advantages of reduced operative times and reduced blood loss. Further, anterior procedures do not interfere with the posterior anatomic structure of the lumbar spine. Anterior procedures also minimize scarring within the spinal canal while still achieving improved fusion rates, which is advantageous from a structural and biomechanical perspective. These generally preferred anterior procedures are particularly advantageous in providing improved access to the disc space, and thus correspondingly better endplate preparation.

There are a number of problems, however, with traditional spinal implants including, but not limited to, improper seating of the implant, implant subsidence (defined as sinking or settling) into the softer cancellous bone of the vertebral body, poor biomechanical integrity of the endplates, damaging critical bone structures during or after implantation, and the like. In summary, at least ten, separate challenges can be identified as inherent in traditional anterior spinal fusion devices. Such challenges include: (1) end-plate preparation; (2) implant difficulty; (3) materials of construction; (4) implant expulsion; (5) implant subsidence; (6) insufficient room for bone graft; (7) stress shielding; (8) lack of implant incorporation with vertebral bone; (9) limitations on radiographic visualization; and (10) cost of manufacture and inventory.

With regard to manufacturing of such implants, there are traditionally many steps necessary to produce a high quality implant. For example, the method or process may require a series of steps including, but not necessarily limited to, cutting the basic implant shape from raw materials and then sequentially adding features by removing material from the initial basic shape. Thus, such methods may include numerous steps of holding and releasing the part until the finished implant is completed. In addition, the parts may undergo subsequent surface processing to provide surface enhancements on the completed implant. The location of such surface enhancements may be limited by the capabilities of the manufacturing process, the resulting surfaces may be non-uniform or inconsistent providing low yields, and the process may require hand processing or costly machining steps in order to provide high-quality implants meeting all required specifications.

SUMMARY OF THE INVENTION

The present invention provides for interbody spinal implants produced by simplified and optimized methods, which allow each step to be utilized without constraining the subsequent processes or degrading the previous process steps. The process of the present invention can use the same raw materials as traditional implant manufacturing methods, but with fewer process steps and fewer transitions during the manufacturing process. The dimensions and surface features of the implant may be produced in a more accurate and repeatable fashion. In addition, the need for hand processing or special machining can be minimized or eliminated. For at least these reasons, the production time and costs may also be reduced in producing the implants.

In one embodiment, the present invention provides a method of producing an interbody spinal implant including obtaining a blank (e.g., from a supplier or manufacturing the blank from raw materials) comprising a top surface, a bottom surface, opposing lateral sides, and opposing anterior and posterior portions, and applying a subtractive process, such as masked acid etching, to at least a portion the top surface, the bottom surface, or both surfaces of the blank to form a roughened surface topography. After the subtractive process, the blank is machined (e.g., milled, turned, or the like) to form an interbody spinal implant. The interbody spinal implant has a body with a top surface and a bottom surface, where the top surface, the bottom surface, or both surfaces of the interbody spinal implant have the roughened surface topography formed by the subtractive process. The implant also includes opposing lateral sides and opposing anterior and posterior portions—all formed from the blank. The implant is also machined to have a substantially hollow center, and a single vertical aperture (a) extending from the top surface to the bottom surface of the body, (b) having a size and shape predetermined to maximize the surface area of the top surface and the bottom surface available proximate the anterior and posterior portions while maximizing both radiographic visualization and access to the substantially hollow center, and (c) defining a transverse rim. The implant may be machined to have additional features, such as at least one transverse aperture, one or more holes, and the like.

The roughened surface topography preferably includes a regular repeating pattern. The regular repeating pattern may help to promote bone growth, fusion, and healing responses and may be oriented in opposition to the biologic forces on the interbody spinal implant and to an insertion direction. The regular repeating pattern may be formed using mask techniques as the subtractive process. Therefore, the subtractive process may include applying a maskant (e.g., by sputtering, deposition, evaporation, or the like) to the top surface, bottom surface, or both surfaces of the blank. After the maskant is applied and cured, the subtractive process may include, for example, applying an acid etching solution (e.g., by spraying, immersion, or the like) to the unmasked surfaces. Once etched, a single time or repeatedly, the maskant may then be removed to reveal the roughened surface topography. The blank now having the roughened surface topography on the top, bottom, or both surfaces can then be machined into the appropriate implant shapes and including any apertures, holes, and the like.

Various implant body shapes are provided to allow for implantation through various access paths to the spine through a patient's body. The structures and surfaces are designed to work in concert to preserve endplate bone structures, provide for sufficient bioactivity in each respective location, and provide stability within the disc space and the graft containment axial column. In particular, the shapes and textures of the bioactive surfaces vary based on the implant insertion path, location within the disc space, and frictional characteristics of the surfaces.

The methods may also include other steps, such as machining the blank to have a slope or angle (e.g., a lordosis angle); cutting the blank to implant width before machining the blank to form the interbody spinal implant; and subjecting at least one surface of the interbody spinal implant, once formed, to nano processing (e.g., mild chemical etching, laser or other directed energy material removal, abrasion, blasting, tumbling, or the like).

In another embodiment, a method of producing a composite interbody spinal implant includes obtaining a blank comprising a top surface, a bottom surface, opposing lateral sides, and opposing anterior and posterior portions; applying a subtractive process to at least a portion of the top surface of the blank to form a roughened surface topography; and subsequently machining the blank to form an integration plate. The integration plate has a top surface comprising an integration surface with the roughened surface topography, a bottom surface, opposing lateral sides, opposing anterior and posterior portions, and a single vertical aperture extending from the top surface to the bottom surface. One or two integration plates may be combined and assembled with a separate body to form a composite interbody spinal implant. The body has a top surface, a bottom surface, opposing lateral sides, opposing anterior and posterior portions, a substantially hollow center, and a single vertical aperture extending from the top surface to the bottom surface of the body. The integration plate(s) and the body are assembled to align the components. In particular, the single vertical aperture of the integration plate is aligned with the single vertical aperture of the body such that the integration plate does not extend beyond the outer circumference of the body.

The implant body, the integration plate or plates, or both components may be fabricated from a metal. A preferred metal is titanium or a titanium alloy. In the case of a composite implant, the implant body may be fabricated from a metal or a non-metallic material.

The resulting implant, for a solid body implant or a composite implant, comprises at least one integration surface having a roughened surface topography where the entire implant or the integration plate was produced by such a process that the surfaces and edges of the implant are of high quality and reliability. Thus, the resulting surfaces are uniform and consistent providing high yields, the locations of the surface enhancements are not limited and are not degraded by subsequent processing, and the process does not require hand processing or costly machining in order to meet all required specifications.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIGS. 3A and 3B show a blank in the form of a bar with a lordis angle implant height;

FIG. 7B shows a top view of the embodiment of the interbody spinal implant illustrated in FIG. 7A;

DETAILED DESCRIPTION OF THE INVENTION

The present invention provides for interbody spinal implants, including solid body implants and composite implants, produced by fewer process steps and fewer transitions during the manufacturing process. The dimensions and surface features of the implant may be produced in a very accurate and repeatable manner without bleeding (e.g., bleeding of the acid etchant) or poor quality at the edges or interfaces between areas with different surface features (e.g., roughened topography versus substantially smooth surfaces).

Figure 2:
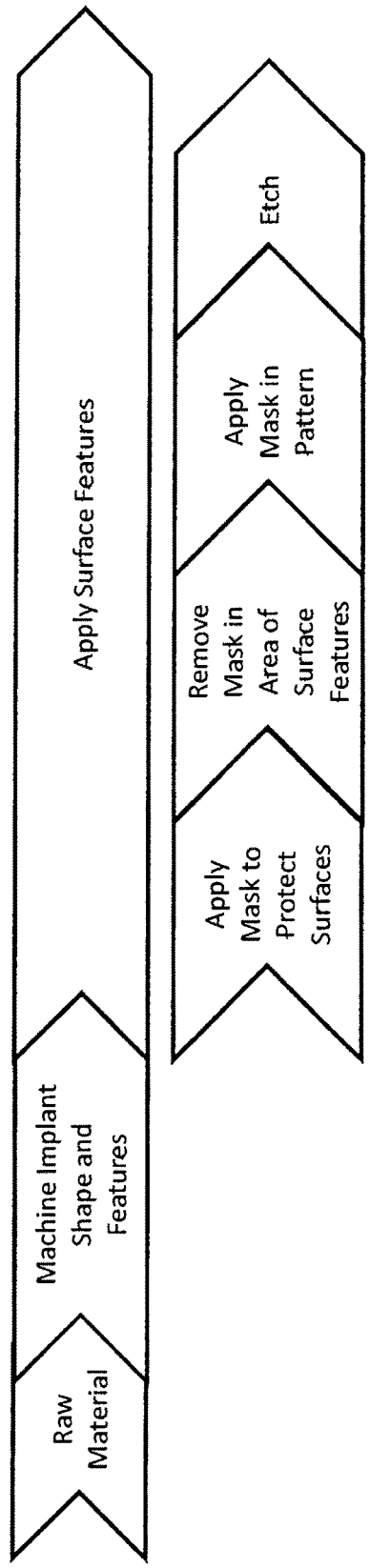
FIG. 2 shows a process flowchart according to one method of producing implants.

Under common manufacturing techniques, an implant may be produced by machining the implant from a raw material and, after the implant is produced, applying any surface processing to the surfaces requiring such treatment. Referring to the drawing, in which like reference numbers refer to like elements throughout the various figures that comprise the drawing, FIG. 2 depicts a process flowchart according to one method of producing implants. For example, the raw material may be obtained from a supplier, and machined into the basic implant shape with certain features (e.g., holes). After machining the implant, certain surface features may be applied to desired surfaces. For example, FIG. 2 shows a method where a mask is applied to protect the surfaces of the implant (i.e., a protective maskant). Those protected surfaces will not undergo any surface treatment. The protective mask may be applied to the entire implant (e.g., by immersion in the maskant). Then, a portion of the protective mask may be removed, often cut by hand, to expose the area of the implant which requires a special surface treatment. Once the given area is exposed and unmasked, another mask may be applied to the exposed surface, for example, in a desired pattern. The surface may then undergo a surface treatment, such as acid etching, to remove the base material. It is possible that the surface could undergo repeated etchings. Therefore, the protective maskant must survive and protect the protected surfaces from such treatments, even if repeated several times. Problems arise, however, because the maskant may not provide good protection especially for repeated treatments or may start to bleed the etchant at the edges where the unprotected areas adjoin the protective maskant portions. If the etchant bleeds under the protective maskant, the bleed may produce holes or defects in undesired areas rendering the entire part worthless. In addition, because the protective maskant covering the surface to be treated is often removed by hand, there is a high likelihood of variability and inconsistency in the etching results.

Figure 1:
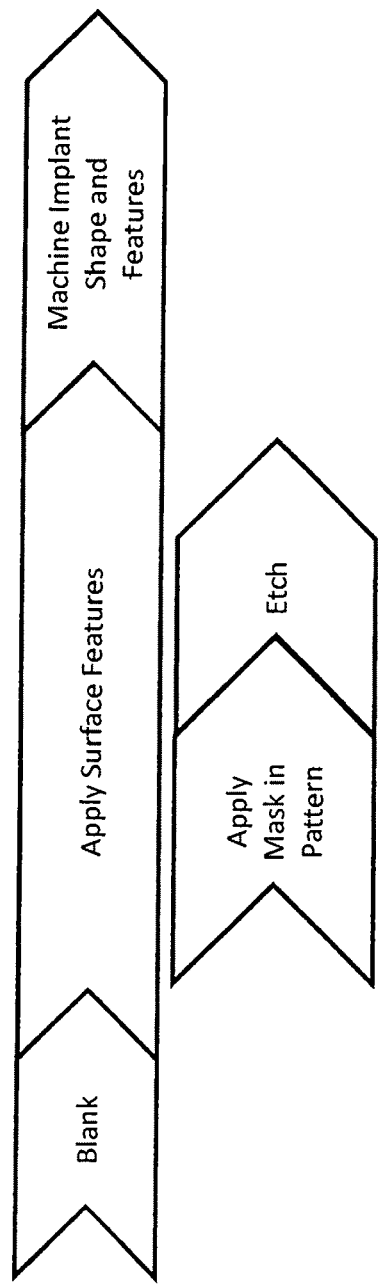
FIG. 1 shows a process flowchart according to one embodiment of the invention.

Accordingly, in one embodiment of the present invention, a method of producing an interbody spinal implant includes obtaining a blank, applying a subtractive process to form a roughened surface topography on a surface of the blank, and, after the subtractive process, machining the blank to form an interbody spinal implant. FIG. 1 depicts an exemplary embodiment of a process flowchart according to the invention. First, a blank is obtained or created. Then, the surface features are applied to the desired surface. For example, the mask is applied in a desired pattern and then an acid etch is applied. The etchant may even be applied repeatedly without worry of harming the other implant surfaces. After the surface treatment is applied, then the blank is machined into individual implants. The machining reveals inner areas of the blank which were not exposed to the subtractive process (e.g., the lateral sides 30, the anterior portion 40, and the smooth rounded edge 7). Accordingly, there is no likelihood of bleed or other defects in those areas. There is also no need to apply a protective maskant over the entire implant surface or to use hand processing or special equipment to remove portions of a protective maskant.

FIGS. 3A and 3B show an example of a blank 6. The blank 6 may obtained or supplied, for example, in a bar shape (e.g., a substantially rectangular shape). It should be understood, however, that any suitable shape for the blank 6 may be selected based on the ultimate implant shape desired. For example, the blank 6 may be obtained from a raw material or part supplier or may be machined into the desired shape. Also, the blank 6 may be obtained by manufacturing (e.g., machining) raw materials typically used to construct the implants in a traditional process, such as titanium bars. The blank 6 comprises a top surface 16, a bottom surface 26, opposing lateral sides 36, and opposing anterior portions 46 and posterior portions 56, which may generally correspond with the positions of the resulting implant 1 or integration plate 82 made from the blank 6. The blank 6 may be in the form of a bar with a length L which allows for production of more than one implant from a single blank 6.

The blank 6 and the resulting implant 1 may also be produced in other suitable shapes. In particular, the top surface 16, the bottom surface 26, or both surfaces of the blank 6 (and ultimately the implant 1) may include curvatures, convexities, slopes, angles, radii, or compound surfaces. For example, the top surface 16 and bottom surface 26 of the blank 6 corresponding to the top surface 10 and bottom surface 20 of the implant 1 may include a convex curve, a concave curve, an angle, a tail, or a compound surface containing one or more of these types of surfaces.

In an exemplary embodiment, the blank 6 is machined to have a lordosis angle A. As will be well recognized by one of ordinary skill in the art, lordosis is curvature of a portion of the lumbar or cervical vertebral column. FIG. 3A shows the lordosis angle A of the blank 6 may be provided with respect to the height of the blank 6. For example, the anterior portion 46 of the blank 6 may have a higher height that the posterior portion 56, which provides a lordosis angle A. As much as fifteen degrees of lordosis (or more) may be built into the blank 6 (and ultimately the implant) to help restore cervical balance. For example, the lordosis angle A may be between about 1-15 degrees, about 3-7 degrees, or any other degree of lordosis as is needed.

Figure 14:
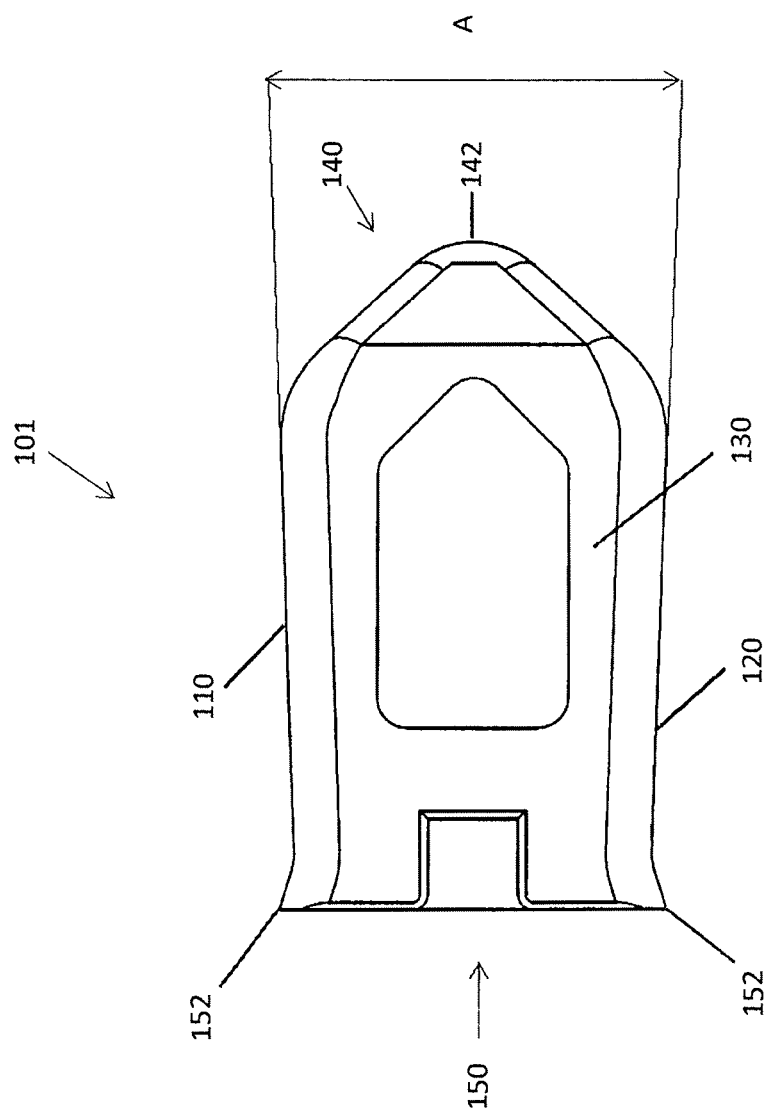
FIG. 14 shows a side view of one embodiment of an implant having a lordosis angle and a tail.

As shown in FIG. 14, the implant 101 may comprise a tail 152 proximate the posterior portion 150, which is formed from a blank 6 (not shown) having a tail (e.g., proximate the posterior portion 56 of the blank 6). The tail 152 is preferably greater in height than the shortest distance between the top surface 110 and the bottom surface 120 of the implant 101. In one embodiment, the tail 152 is equal to or greater in height than the remainder of the implant 101. FIG. 14 also shows a compound surface having both a lordosis angle A (e.g., about a 4 degree lordosis angle A) and a tail 152 on the top surface 110 and the bottom surface 120 proximate the posterior portion 150 of the implant 101. The compound surface is preferably obtained from a blank 6 (not shown) having both a lordosis angle A and a tail on the top surface 16 and the bottom surface 26. The tail 152 may function, for example, as an anti-expulsion feature once the implant 101 is inserted into position.

Figure 15:
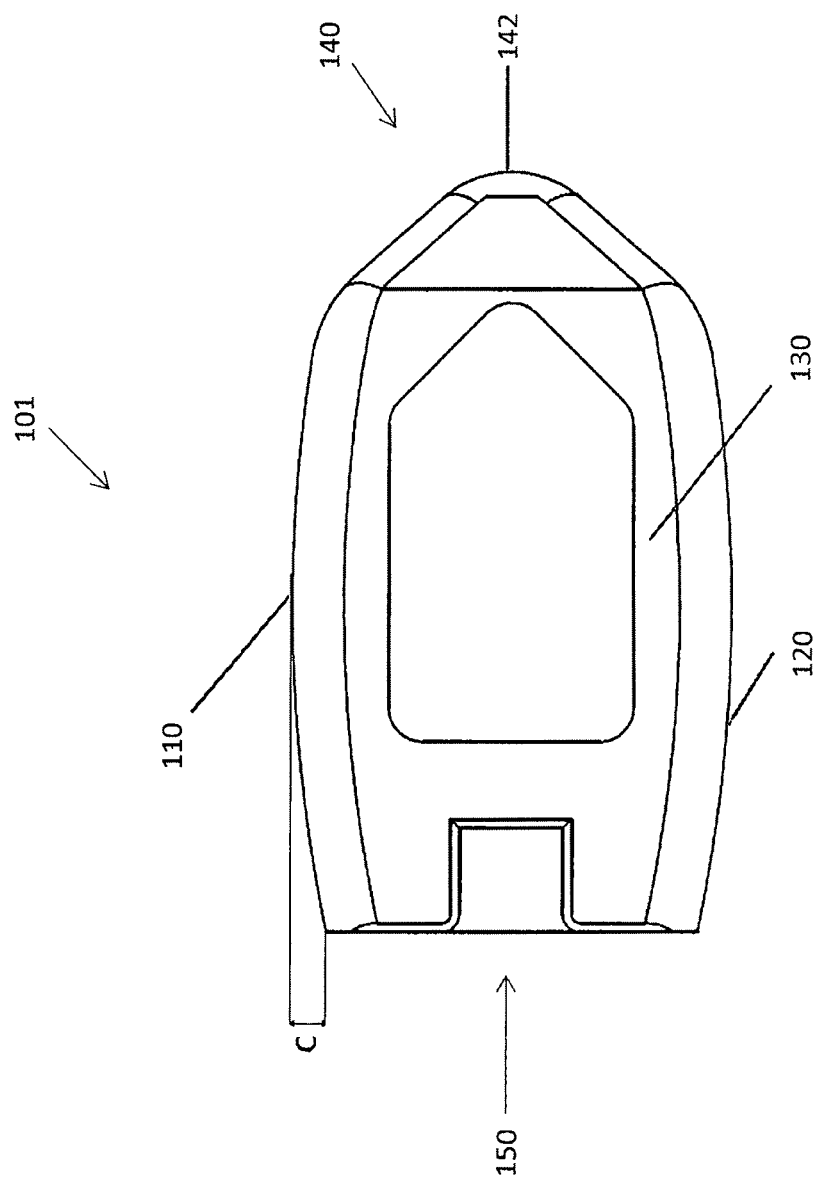
FIG. 15 shows a side view of one embodiment of an implant having a convex top and bottom surface.

In another embodiment, the blank 6 is machined to have a convex curve on the top surface 16, the bottom surface 26, or both surfaces of the blank 6 (not shown). FIG. 15 depicts an implant 101 that may be obtained from such a blank 6 machined with convex curves where the top surface 110 and the bottom surface 120 of the implant 101 each have a convex curve. The convex curve has a maximum height C substantially at the center point of the top surface 110 and the bottom surface 120. The maximum height C may provide for any desired degree of curvature. For example, the maximum height C may be about one mm as compared with the posterior portion 150. It is also contemplated that the maximum height C of the curve may be at any point, not necessarily the midpoint, along the top surface 110 or the bottom surface 120 of the implant 101. The implants depicted in FIGS. 14 and 15 may be particularly well suited for Posterior Lumbar Interbody Fusion (PLIF).

The blank 6 may be composed of any suitable material. In a preferred embodiment, the blank 6 is comprised of a metal. Suitable metals, such as titanium, aluminum, vanadium, tantalum, stainless steel, and alloys of those metals, may be selected by one of ordinary skill in the art. In a preferred embodiment, the metal is at least one of titanium, aluminum, and vanadium, without any coatings. In a more preferred embodiment, the blank 6 is comprised of titanium or a titanium alloy.

A subtractive process is applied to at least one surface of the blank 6. As used in this document, "subtractive process" is intended to encompass any process which removes material from a surface of the blank 6. Suitable subtractive techniques may include for example, machining (e.g., machine tools, such as saws, lathes, milling machines, and drill presses, are used with a sharp cutting tool to physically remove material to achieve a desired geometry), unmasked or masked etching (e.g., portions of the surface are protected by a masking material which resists etching and an etching substance is applied to unmasked portions), and the like. The subtractive process may include a single subtractive step or multiple subtractive steps.

The subtractive process may include a masking step before the subtractive step or steps. In other words, a mask may be applied to the desired surface, for example, to produce a pattern (e.g., dots, circles, squares, lines, or amorphous shapes) before implementing the subtractive technique. The maskant may be applied using any suitable techniques known in the art, such as deposition (e.g., sputter deposition, vacuum deposition, physical vapor deposition, chemical vapor deposition, and spin coating) and evaporation (e.g., electron beam evaporation, thermal evaporation, and plasma assisted thermal evaporation). The sputtering may include, for example, DC sputtering, DC magnetron sputtering, AC sputtering, pulse DC sputtering, RF sputtering, and the like. In an exemplary embodiment, a maskant is applied in a regular pattern using a sputtering technique, for example, using an ink jet printing apparatus. A suitable maskant (e.g., a polymeric maskant) may be selected by one of ordinary skill in the art depending on the subtractive process employed. The maskant may be cured, for example, at room temperature or under heating. Once the subtractive process is complete and the pattern has been formed and cut into the blank 6, the maskant or maskants may be removed using any suitable mechanisms (e.g., solvent removal).

In an exemplary embodiment, the subtractive process is applied to at least one of the surfaces which will become the integration surfaces of the resulting implant 1. As used in this document, the integration surface is the surface at least partially in contact with the vertebral or bone structure. In particular, the subtractive process may be applied to the top surface 16 of the blank 6, the bottom surface 26 of the blank 6, or both surfaces.

The subtractive process ultimately results in one or more integration surfaces on the implant 1 having predefined surface features that (a) engage the vertebral endplates with a friction fit and, following an endplate preserving surgical technique, (b) attain initial stabilization, and (c) benefit fusion. The composition of the endplate is a thin layer of notch-sensitive bone that is easily damaged by features (such as teeth) that protrude sharply from the surface of traditional implants. Avoiding such teeth and the attendant risk of damage, the roughened surface topography 80 of the integration surface(s) does not have teeth or other sharp, potentially damaging structures; rather, the roughened surface topography 80 may have a pattern of repeating features of predetermined sizes, smooth shapes, and orientations. As used in this document, "predetermined" means determined beforehand, so that the predetermined characteristic must be determined, i.e., chosen or at least known, before use of the implant 1.

These designed surfaces are composed of various sizes of features that, at the microscopic level, interact with the tissues and stimulate their natural remodeling and growth. At a larger scale these features perform the function of generating non-stressful friction that, when combined with a surgical technique that retains the most rigid cortical bone structures in the disc space, allow for a friction fit that does not abrade, chip, perforate, or compromise the critical endplate structures. The features may be divided into three size scales: nano, micro, and macro. The overlapping of the three feature sizes can be achieved using manufacturing processes that are completed sequentially and, therefore, do not remove or degrade the previous method.

Figure 4B:
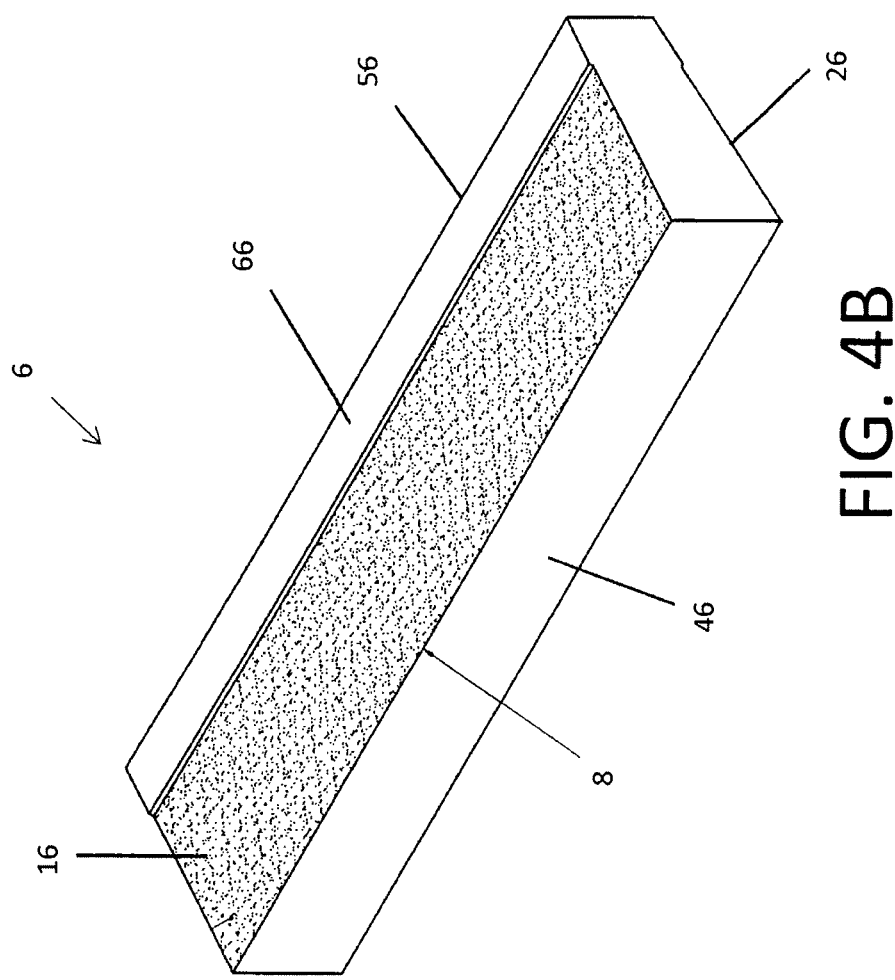
FIGS. 4A and 4B show the resulting bar profile after etching and a residual handle formed from the un-etched surfaces.
Figure 4A:
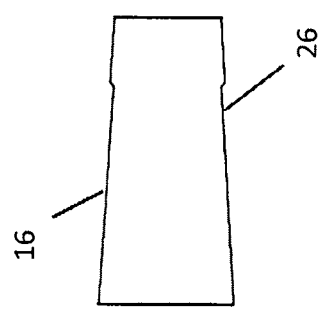

The subtractive process may be applied to the entire surface or a portion thereof of the blank 6. As depicted in FIGS. 4A and 4B, the subtractive process may be applied to the portion of the blank 6 which will be formed into the implant 1 or integration plate 82. The subtractive process may be used over the entire blank 6 or any portion thereof because the implant 1 or integration plate 82 will ultimately be machined from the blank 6 and the machining will reveal inner portions of the blank 6 not exposed to such subtractive techniques (e.g., a substantially smooth rounded edge 7). In other words, there is no concern about etching unmasked areas and no need to provide a protective mask to protect certain surfaces. From a process optimization standpoint, however, it may be preferable to only apply the subtractive process to the desired surfaces. FIG. 4B depicts a region on the posterior portion 56 of the blank 6 extending from one lateral side 36 to the other which is not subjected to the subtractive process. As shown in FIG. 4A, this may result in a profile where the blank 6 is etched to the implant finish height and an un-etched portion along the posterior portion 56 remains to function as a handle 66 in the subsequent machining operations. The blank 6 may also comprise a finished trimmed edge which is very consistent and may ultimately function as the expulsion edge 8 in the implant 1 once formed.

The subtractive process may include macro processing, micro processing, or both. The term "macro" typically means relatively large; for example, in the present application, dimensions measured in millimeters (mm). The term "micro" typically means one millionth ($10^{-6}$); for example, in the present application, dimensions measured in microns (μm) which correspond to $10^{-6}$ meters.

The macro processing may include mechanical (e.g., machining though conventional processes) or chemical bulk removal, for example, to generate macro features. The macro features may be of any suitable shape, for example, roughly spherical in shape, without undercuts or protruding sharp edges. Other shapes are possible, such as ovals, polygons (including rectangles), and the like. These features may be at least partially overlapped with other surface features using either chemical or mechanical methods (e.g., $AlO_2$ blasting) in predetermined patterns which do not result in undercuts or protruding sharp edges.

Figure 16:
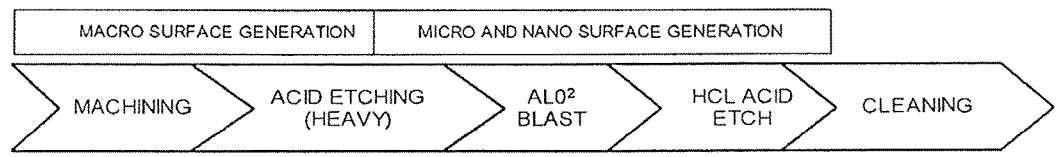
FIG. 16 illustrates one set of process steps that can be used to form macro, micro, or nano processes.

FIG. 16 illustrates one set of process steps that can be used to form macro, micro, or nano processes. As illustrated, there may be some overlap in the processes that can be applied to form each of the three types of features (macro, micro, and nano). For example, acid etching can be used to form the macro features, then the same or a different acid etching process can be used to form the micro features. The features may be provided in a random design or a predetermined pattern (e.g., a repeating pattern).

The macro features are relatively large features (e.g., on the order of millimeters). The macro features may be formed from subtractive techniques (e.g., mechanical or chemical bulk removal, for example) or additive techniques (e.g., deposition). Preferably, the macro features are formed by subtractive techniques, which remove at least portions of the surface (e.g., from the titanium material that was used to form the blank 6). Suitable subtractive techniques may include, for example, machining (e.g., machine tools, such as saws, lathes, milling machines, and drill presses, are used with a sharp cutting tool to physically remove material to achieve a desired geometry) or unmasked or masked etching (e.g., portions of the surface are protected by a masking material which resists etching and an etching substance is applied to unmasked portions). The patterns may be organized in regular repeating patterns and optionally overlapping each other.

Depending on the surface structure desired, the micro surface features (e.g., on the order of micrometers) may be applied to all or a portion of the surface (for example, to the surface that will ultimately form the integration surface). The micro features may also be formed from subtractive techniques (e.g., mechanical or chemical bulk removal, for example) or additive techniques (e.g., deposition). Preferably, the micro features are also formed by subtractive techniques.

In an exemplary embodiment, the micro features are cut by masked or unmasked etching, such as acid etching. For example, portions of the surface, optionally including portions of the surface exposed by the macro processing described, may be exposed to a chemical etching. The subtractive process may comprise a single step or multiple steps. For example, the subtractive process may include about two to four sequential steps of acid etching.

In a preferred embodiment, the subtractive process comprises or consists of the micro process. Most preferably, the subtractive process includes acid etching, with a strong or weak acid, such as hydrochloric acid (HCl), hydroiodic acid (HI), hydrobromic acid (HBr), hydrofluoric (HF), perchloric acid ($HClO_4$), nitric acid ($HNO_3$), sulfuric acid ($H_2SO_4$), and the like. The etching process may be repeated a number of times as necessitated by the amount and nature of the irregularities required for any particular application. Control of the strength of the etchant material, the temperature at which the etching process takes place, and the time allotted for the etching process—all allow fine control over the resulting surface produced by the process. The number of repetitions of the etching process can also be used to control the surface features. For example, the micro features may be obtained via the repetitive masking and chemical or electrochemical milling processes described in U.S. Pat. No. 5,258,098; U.S. Pat. No. 5,507,815; U.S. Pat. No. 5,922,029; and U.S. Pat. No. 6,193,762, the contents of which are incorporated by reference into this document, in their entirety, and for all purposes.

The acid solution may be applied to the surface (e.g., a treated surface) of the blank 6 using any suitable mechanism or techniques known in the art, for example, immersion, spraying, brushing, and the like. In an exemplary embodiment, the acid solution is applied to the surface by immersing the entire blank 6 in the solution. If desired, certain areas of the surface or the blank 6 may be masked. After the acid solution is applied, the acid solution may be removed, for example, by rinsing with water (e.g., deionized water). The treated surface or the entire blank 6 may be subsequently dried. The treated surface may be dried using any suitable mechanism or techniques known in the art, for example, by heating in an oven (e.g., a dry oven).

By way of example, an etchant mixture of at least one of nitric acid and hydrofluoric acid may be repeatedly applied to a titanium surface to produce an average etch depth of about 0.53 mm. In another example, chemical modification of a titanium surface can be achieved using at least one of hydrofluoric acid, hydrochloric acid, and sulfuric acid. In a dual acid etching process, for example, the first exposure may be to hydrofluoric acid and the second may be to a hydrochloric acid and sulfuric acid mixture. Chemical acid etching alone may enhance osteointegration without adding particulate matter (e.g., hydroxyapatite) or embedding surface contaminants (e.g., grit particles).

The micro features may also be cut by abrasive or grit blasting, for example, by applying a stream of abrasive material (such as alumina, sand, and the like) to the surface. The abrasive material may include inert and non-bioactive materials. Alternatively, the abrasive material may include those materials reactive with biological functions as part of healing and fusions. In an exemplary embodiment, the micro features are created, at least partially, with an aqueous hydrochloric acid etching step and optionally at least partially with an $AlO_2$ blasting step. Patterns may be organized in regular repeating patterns and optionally overlapping each other.

The subtractive process forms a roughened surface topography 80. The shapes of the frictional surface protrusions of the roughened surface topography 80 are formed using processes and methods commonly applied to remove metal during fabrication of implantable devices such as chemical, electrical, electrochemical, plasma, or laser etching; cutting and removal processes; casting; forging; machining; drilling; grinding; shot peening; abrasive media blasting (such as sand or grit blasting); and combinations of these subtractive processes. Additive processes such as welding, thermal, coatings, sputtering, and optical melt additive processes may also be suitable. The resulting surfaces either can be random in the shape and location of the features or can have repeating patterns. This flexibility allows for the design and production of surfaces that resist motion induced by loading in specific directions that are beneficial to the installation process and resist the opposing forces that can be the result of biologic or patient activities such as standing, bending, or turning or as a result of other activities. The shapes of the surface features work to increase the surface contact area but do not result in undercuts that generate a cutting or aggressively abrasive action on the contacting bone surfaces.

Figure 5B:
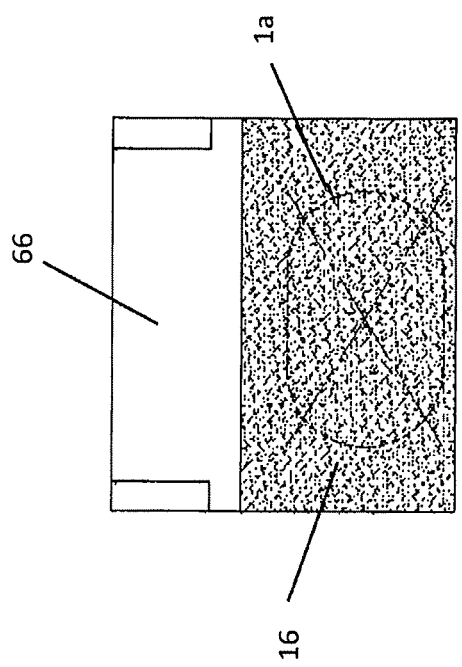
FIGS. 5A and 5B show the blank after etching where the blank is cut to implant width.
Figure 5A:
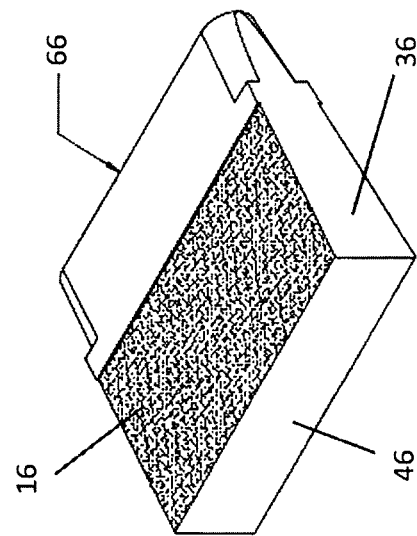
Figure 6:
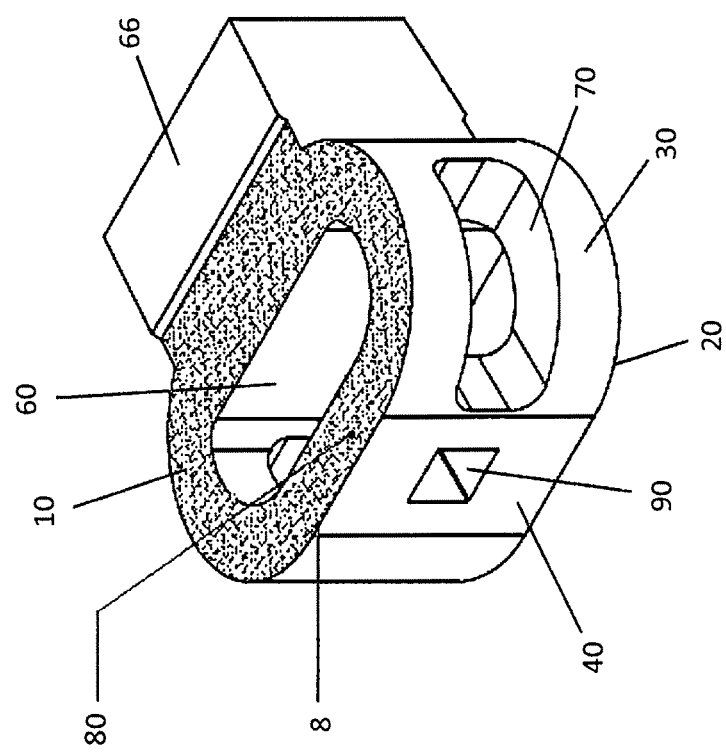
FIG. 6 shows a perspective view of an embodiment of the interbody spinal implant after machining with the handle still attached.

After the subtractive process, the blank 6 is machined to form an interbody spinal implant 1 or a portion of the implant 1 (e.g., an integration plate 82). FIG. 5A shows the implant footprint 1 a to be machined from the etched bar. The features of the implant 1 or the integration plate 82 may be machined using typical equipment and techniques known in the art (e.g., by milling, turning, combinations of the two, or the like). Prior to cutting or removing the features of the implant 1 (the apertures, holes, etc.), the length L of the blank 6 may first be cut down to implant width. As shown in FIG. 6, the blank 6 may be manipulated using the handle 66, which may be removed after the implant 1 is formed. Because the implant 1 is machined from the etched blank 6, there are no extra process steps necessary to mask or protect certain areas of the implant 1 for special surface treatment. Moreover, there are no bleed or unwanted surface defects because the roughened surface 80 already exists on the implant 1 and does not need to be applied later.

Figure 7A:
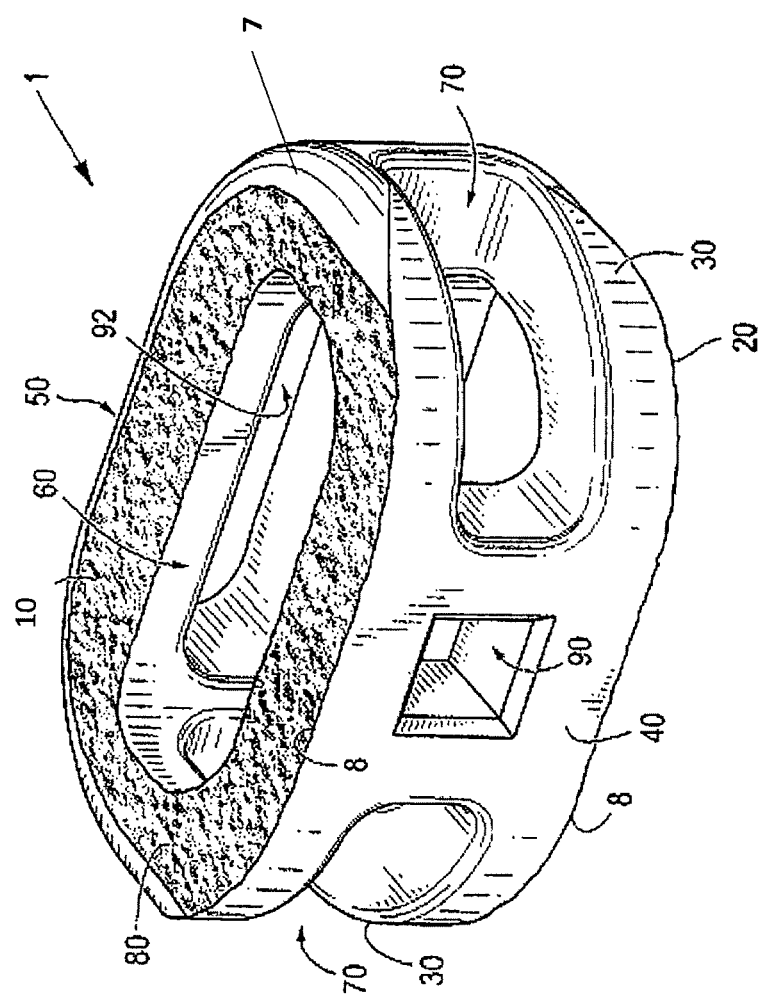
FIG. 7A shows a perspective view of an embodiment of the interbody spinal implant having a generally oval shape and roughened surface topography on the top surface.

FIG. 6 show a perspective view of a first embodiment of the interbody spinal implant 1 in process, and FIG. 7A show a perspective view of the resulting interbody spinal implant 1, which is especially well adapted for use in an Anterior Lumbar Interbody Fusion (ALIF) procedure. The interbody spinal implant 1 includes a top surface 10, a bottom surface 20, opposing lateral sides 30, and opposing anterior portions 40 and posterior portions 50. The interbody spinal implant 1 may include implants made of a single piece of material or composite implants.

Interbody spinal implants 1 made of a single piece of material or solid-body implants do not include integration plates 82. Thus, the entire implant 1 is machined directly from a single blank 6. The integration surface may include the top surface 10 of the implant 1, the bottom surface 20 of the implant 1, or both surfaces. The integration surfaces have a roughened surface topography 80, without sharp teeth that risk damage to bone structures, and were formed in the subtractive process described above.

Figure 8:
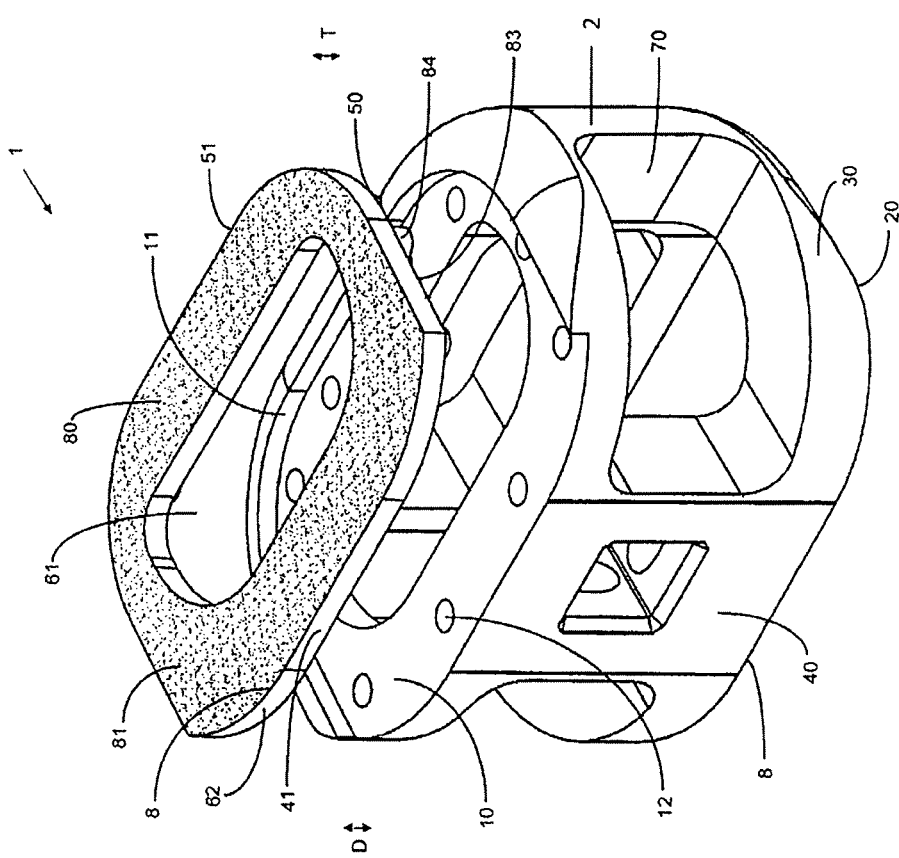
FIG. 8 shows an exploded view of a generally oval-shaped implant with an integration plate.
Figure 9:
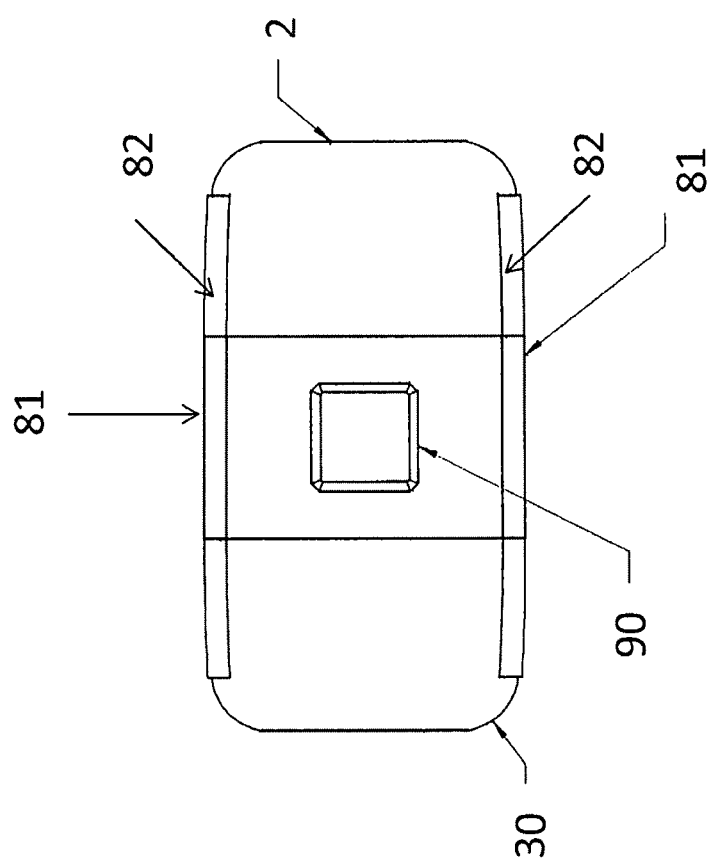
FIG. 9 shows an anterior view of an embodiment of the interbody spinal implant having two integration plates, which sandwich the body of the implant.

Composite implants include at least a body 2 and one or two integration plates 82, which may be formed from the same or different materials. The one or two integration plates 82 are machined directly from the blank 6 and the body 2 may be machined separately. The integration surfaces have a roughened surface topography 80, without sharp teeth that risk damage to bone structures, and were formed in the subtractive process. As depicted in FIG. 8, the implant 1 includes a first integration plate 82 affixed to the top surface 10 of the body 2 and an optional second integration plate 82 (shown in FIG. 9) affixed to the bottom surface 20 of the body 2. The first integration plate 82 and optional second integration plate 82 each have a top surface 81, a bottom surface 83, opposing lateral sides, opposing anterior portion 41 and posterior portion 51, and a single vertical aperture 61 extending from the top surface 81 to the bottom surface 83 and aligning with the single vertical aperture 60 of the body 2.

When present, the integration plates 82 comprise an integration surface (e.g., the top surface 81 of the integration plate 82), which is adapted to grip bone through friction generated when the implant 1 is placed between two vertebrae and to inhibit migration of the implant 1 once implanted. The integration surfaces may also have a fusion and biologically active surface geometry. In other words, at least a portion of the top surface 81 of the first integration plate 82 (e.g., a first integration surface) and optionally a top surface 81 of a second integration plate 82 (e.g., a second integration surface) has a roughened surface topography 80, without sharp teeth that risk damage to bone structures. The roughened surface topography 80 preferably includes micro features of a regular repeating pattern, formed during the subtractive process, which may promote biological and chemical attachment or fusion with the bone structure.

The body 2 and at least one integration plate 82 are preferably compatibly shaped, such that the implant 1 having the body 2 and integration plate(s) 82 joined together may have a generally oval shape, a generally rectangular shape, a generally curved shape, or any other shape described or exemplified in this specification. Thus, for example, the body 2 and the integration plate(s) 82 may be generally oval-shaped in transverse cross-section. The body 2 and the integration plate(s) 82 may be generally rectangular-shaped in transverse cross-section. The body 2 and the integration plate(s) 82 may be generally curved-shaped in transverse cross-section.

The body 2 and integration plate(s) 82 of the implant 1 may be the same material or may be different materials. The body 2 and the integration plate(s) 82 may be composed of a suitable biocompatible material. In an exemplary embodiment, the body 2 and optional integration plate(s) 82 are formed of metal, which may be coated or not coated. Suitable metals, such as titanium, aluminum, vanadium, tantalum, stainless steel, and alloys of the metals, may be selected by one of ordinary skill in the art. In a preferred embodiment, however, the metal is at least one of titanium, aluminum, and vanadium, without any coatings. In a more preferred embodiment, the body 2 and optional integration plate(s) 82 are comprised of titanium or a titanium alloy. An oxide layer may naturally form on a titanium or titanium alloy.

Alternatively, the body 2 may be composed of a non-metal biocompatible material. In one embodiment, the body 2 of the implant 1 is formed of a plastic, polymeric, or composite material. For example, suitable polymers may comprise silicones, polyolefins, polyesters, polyethers, polystyrenes, polyurethanes, acrylates, and co-polymers and mixtures of the polymers. Certain embodiments of the present invention may be comprised of a biocompatible, polymeric matrix reinforced with bioactive fillers, fibers, or both. Certain embodiments of the present invention may be comprised of urethane dimethacrylate (DUDMA)/tri-ethylene glycol dimethacrylate (TEDGMA) blended resin and a plurality of fillers and fibers including bioactive fillers and E-glass fibers. In another embodiment, the body 2 comprises polyetherether-ketone (PEEK), hedrocel, or ultra-high molecular weight polyethylene (UHMWPE). Hedrocel is a composite material composed of carbon and an inert metal, such as tantalum. UHMWPE, also known as high-modulus polyethylene (HMPE) or high-performance polyethylene (HPPE), is a subset of the thermoplastic polyethylene, with a high molecular weight, usually between 2 and 6 million.

Certain embodiments of the interbody spinal implant 1 are substantially hollow and have a generally oval-shaped transverse cross-sectional area. Substantially hollow, as used in this document, means at least about 33% of the interior volume of the interbody spinal implant 1 is vacant. Still further, the substantially hollow portion may be filled with cancellous autograft bone, allograft bone, demineralized bone matrix (DBM), porous synthetic bone graft substitute, bone morphogenic protein (BMP), or combinations of those materials.

Certain embodiments of the present invention may be especially suited for placement between adjacent human vertebral bodies. The implants of the present invention may be used in procedures such as Anterior Lumbar Interbody Fusion (ALIF), Posterior Lumbar Interbody Fusion (PLIF), Transforaminal Lumbar Interbody Fusion (TLIF), and cervical fusion. Certain embodiments do not extend beyond the outer dimensions of the vertebral bodies.

The ability to achieve spinal fusion is directly related to the available vascular contact area over which fusion is desired, the quality and quantity of the fusion mass, and the stability of the interbody spinal implant. Interbody spinal implants, as now taught, allow for improved seating over the apophyseal rim of the vertebral body. Still further, interbody spinal implants, as now taught, better utilize this vital surface area over which fusion may occur and may better bear the considerable biomechanical loads presented through the spinal column with minimal interference with other anatomical or neurological spinal structures. Even further, interbody spinal implants, according to certain aspects of the present invention, allow for improved visualization of implant seating and fusion assessment. Interbody spinal implants, as now taught, may also stimulate osteointegration (e.g., formation of a direct structural and functional interface between the artificial implant and living bone or soft tissue) with the surrounding living bone.

It is generally believed that the surface of an implant determines its ultimate ability to integrate into the surrounding living bone. Without being limited by theory, it is hypothesized that the cumulative effects of at least implant composition, implant surface energy, and implant surface roughness play a major role in the biological response to, and osteointegration of, an implant device. Thus, implant fixation may depend, at least in part, on the stimulation and proliferation of bone modeling and forming cells, such as osteoclasts and osteoblasts and like-functioning cells upon the implant surface. Still further, it appears that these cells attach more readily to relatively rough surfaces rather than smooth surfaces. In this manner, a surface may be bioactive due to its ability to stimulate cellular attachment and osteointegration. The roughened surface topography 80 described in this document may better promote the osteointegration of certain embodiments of the present invention. The roughened surface topography 80 may also better grip the vertebral endplate surfaces and inhibit implant migration upon placement and seating.

Although not necessary, one or more surfaces of the implant 1, including the previously roughened surface topography 80, may undergo further processing after the implant 1 is formed. Depending on the surface structure desired, nano surface features (e.g., on the order of nanometers) may be applied to all or a portion of one or more surfaces of the implant 1. The term "nano" typically means one billionth ($10^{-9}$); for example, in the present application, dimensions measured in nanometers (nm) which correspond to $10^{-9}$ meters. The nano features may also be formed from subtractive techniques (e.g., mechanical or chemical bulk removal, for example) or additive techniques (e.g., deposition). Preferably, the nano features are also formed by subtractive techniques.

In an exemplary embodiment, the nano features are cut by masked or unmasked etching (e.g., chemical etching). In an exemplary embodiment, the nano process also includes an acid etching, with a strong or weak acid, such as hydrochloric acid (HCl), hydroiodic acid (HI), hydrobromic acid (HBr), hydrofluoric acid (HF), perchloric acid ($HClO_4$), nitric acid ($HNO_3$), sulfuric acid ($H_2SO_4$), and the like. The acid etching process for the nano step is preferably less aggressive than the acid etching process in the micro step. In other words, a less acidic, milder, or more diluted acid may be selected. In an exemplary embodiment, the nano features are created, at least partially, with an aqueous hydrochloric acid etching step.

It is contemplated that the nano features may also be created by the abrasive or grit blasting, for example, described for the micro processing step. Patterns may be organized in regular repeating patterns and optionally overlapping each other.

The nano features may also be achieved by tumble finishing (e.g., tumbling) the part or the implant 1. Suitable equipment and techniques can be selected by one of ordinary skill in the art. For example, a barrel may be filled with the parts or implants and the barrel is then rotated. Thus, the parts or implants may be tumbled against themselves or with steel balls, shot, rounded-end pins, ballcones, or the like. The tumbling process may be wet (e.g., with a lubricant) or dry.

As should be readily apparent to a skilled artisan, the process steps described in this document can be adjusted to create a mixture of depths, diameters, feature sizes, and other geometries suitable for a particular implant application. The orientation of the pattern of features can also be adjusted. Such flexibility is desirable, especially because the ultimate pattern of the surface topography desired (for example, the integration surface of the implant 1) may be oriented in opposition to the biologic forces on the implant 1 and to the insertion direction. In one particular embodiment, for example, the pattern of the roughened surface topography 80 may be modeled after an S-shaped tire tread. It is also contemplated that the same or different process steps may be used to create each of the macro, micro, and nano features on each of the desired surfaces.

Several separate parameters can be used to characterize the roughness of an implant surface. Among those parameters are the average amplitude, Ra; the maximum peak-to-valley height, Rmax; and the mean spacing, Sm. Each of these three parameters, and others, are explained in detail below. Surface roughness may be measured using a laser profilometer or other standard instrumentation.

In addition to the parameters Ra, Rmax, and Sm mentioned above, at least two other parameters can be used to characterize the roughness of an implant surface. In summary, the five parameters are: (1) average amplitude, Ra; (2) average peak-to-valley roughness, Rz; (3) maximum peak-to-valley height, Rmax; (4) total peak-to-valley of waviness profile, Wt; and (5) mean spacing, Sm. Each parameter is explained in detail as follows.

1. Average Amplitude Ra

Figure 17:
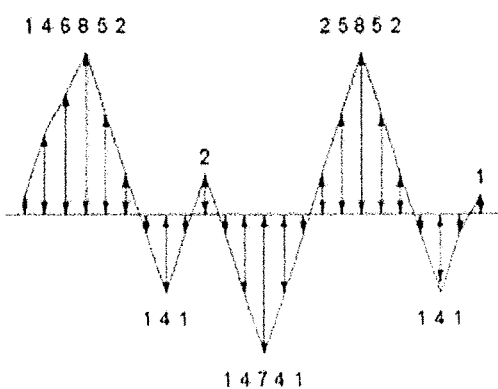
FIG. 17 graphically represents the average amplitude, Ra.

In practice, "Ra" is the most commonly used roughness parameter. It is the arithmetic average height. Mathematically, Ra is computed as the average distance between each roughness profile point and the mean line. In FIG. 17, the average amplitude is the average length of the arrows.

In mathematical terms, this process can be represented as $$Ra = \frac{1}{n}\sum_{i=1}^{n} |y_i|$$

2. Average Peak-to-Valley Roughness Rz

Figure 18:
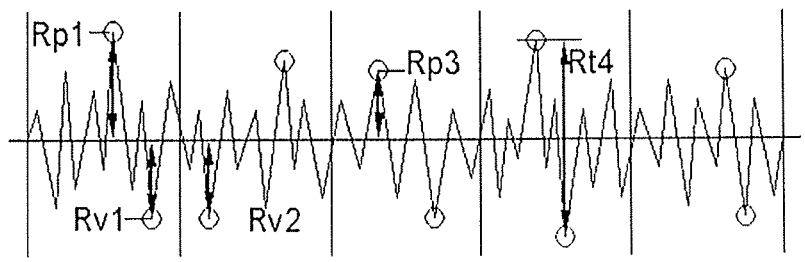
FIG. 18 graphically represents the average peak-to-valley roughness, Rz.

The average peak-to-valley roughness, Rz, is defined by the ISO and ASME 1995 and later. Rz is based on one peak and one valley per sampling length. The RzDIN value is based on the determination of the peak-to-valley distance in each sampling length. These individual peak-to-valley distances are averaged, resulting in the RzDIN value, as illustrated in FIG. 18.

3. Maximum Peak-to-Valley Height Rmax

Figure 19:
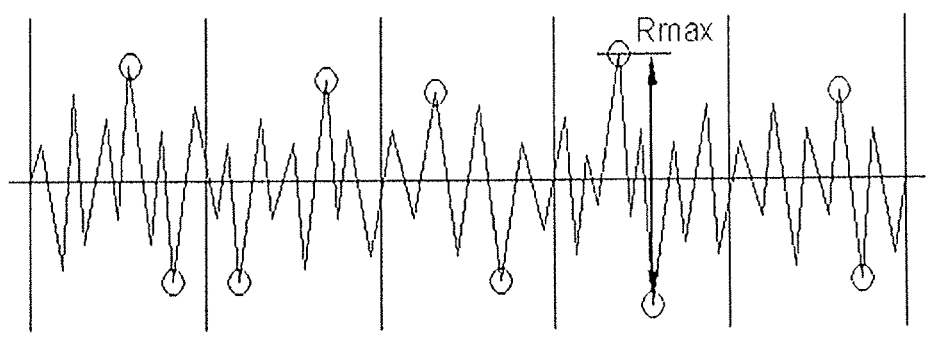
FIG. 19 graphically represents the maximum peak-to-valley height, Rmax.

The maximum peak-to-valley height, Rmax, is the maximum peak-to-valley distance in a single sampling length—as illustrated in FIG. 19.

4. Total Peak-to-Valley of Waviness Profile Wt

Figure 20:
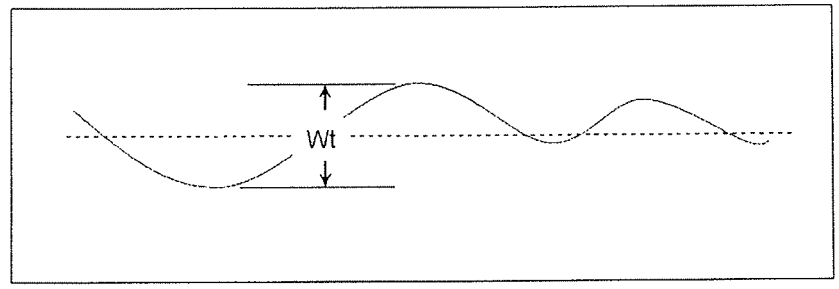
FIG. 20 graphically represents the total peak-to-valley of waviness profile.

The total peak-to-valley of waviness profile (over the entire assessment length) is illustrated in FIG. 20.

5. Mean Spacing Sm

Figure 21:
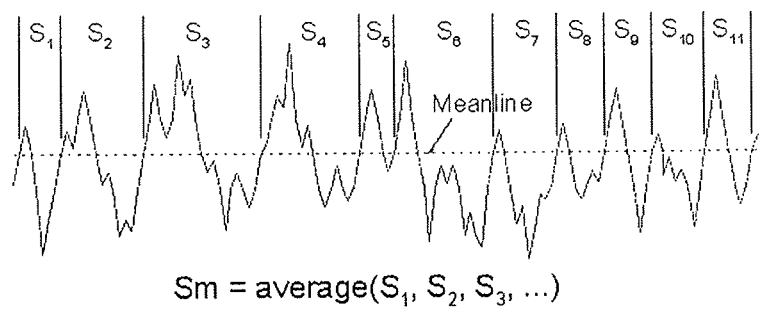
FIG. 21 graphically represents the mean spacing, Sm.

The mean spacing, Sm, is the average spacing between positive mean line crossings. The distance between each positive (upward) mean line crossing is determined and the average value is calculated, as illustrated in FIG. 21.

The parameters Sm, Rmax, and Ra can be used to define the surface roughness following formation of each of the three types of features: macro, micro, and nano.

If present, the following preferred ranges (all measurements in microns) are as follows for the macro features for each of the three parameters. The mean spacing, Sm, is between about 400-2,000, with a range of 750-1,750 preferred and a range of 1,000-1,500 most preferred. The maximum peak-to-valley height, Rmax, is between about 40-500, with a range of 150-400 preferred and a range of 250-300 most preferred. The average amplitude, Ra, is between about 8-200, preferably, 20-200, more preferably 50-150, and most preferably 100-125.

If present, the following preferred ranges (all measurements in microns) are as follows for the micro features for each of the three parameters. The mean spacing, Sm, is between about 20-400, with a range of 100-300 preferred and a range of 200-250 most preferred. The maximum peak-to-valley height, Rmax, is between about 2-40, with a range of 2-20 preferred and a range of 9-13 most preferred. The average amplitude, Ra, is between about 1-20, preferably 2-15, more preferably 4-10, even more preferably 2-8, and most preferably 2-6.

If present, the following preferred ranges (all measurements in microns) are as follows for the nano features for each of the three parameters. The mean spacing, Sm, is between about 0.5-20, with a range of 1-15 preferred and a range of 5-12 most preferred. The maximum peak-to-valley height, Rmax, is between about 0.2-2, with a range of 0.2-1.8 preferred and a range of 0.3-1.3 most preferred. The average amplitude, Ra, is between about 0.01-2, preferably 0.01-1, more preferably, 0.02-0.8, and most preferably 0.03-0.6.

An example of such data is provided in Table 2 below.

TABLE 2

EXAMPLE DATA BY PROCESS STEP

| | Size (Sm) | Depth (Rmax) | Roughness (Ra) |
|---|---|---|---|
| Surface Feature Size and Roughness (Metric): Macro (μm) | | | |
| Max. | 2,000 | 500 | 200 |
| Min. | 400 | 40 | 20 |
| Avg. | 1,200 | 270 | 110 |
| Surface Feature Size and Roughness (Metric): Micro (μm) | | | |
| Max. | 400 | 40 | 20 |
| Min. | 20 | 2 | 1 |
| Avg. | 210 | 11 | 5.5 |
| Surface Feature Size and Roughness (Metric): Nano (μm) | | | |
| Max. | 20 | 2 | 1 |
| Min. | 0.5 | 0.2 | 0.01 |
| Avg. | 10.25 | 1.1 | 0.505 |

In the case of a composite implant 1, 101, 101a, 201, and 301, the integration plate, shown in the drawing as component 82 (FIGS. 8 and 9), 182a (FIG. 10), 182 (FIG. 11), 382 (FIG. 12), and 282 (FIG. 13), respectively, includes the roughened surface topography 80, 180, 180a, 280, and 380 for the integration surface, and is connectable to either or both of the top surface 10, 110, 110a, 210, and 310 or bottom surface 20, 120, 120a, 220, and 320. The integration plate 82, 182, 182a, 282, and 382 includes a top surface 81, 181, 181a, 281, and 381; a bottom surface 83, 183, 183a, 283, and 383; an anterior portion 41, 141, 141a, 241, and 341; a posterior portion 51, 151, 151a, 251, and 351; and at least one vertical aperture 61, 161, 161a, 261, and 361. The anterior portion 41, 141, 141a, 241, and 341 preferably aligns with the anterior portion 40, 140, 140a, 240, and 340 of the main body 2 of the implant 1, 101, 101a, 201, and 301, respectively, and the posterior portion 51, 151, 151a, 251, and 351 aligns with the posterior portion 50, 150, 150a, 250, and 350 of the main body 2 of the implant 1, 101, 101a, 201, and 301, respectively. The vertical aperture 61, 161, 161a, 261, and 361 preferably aligns with the vertical aperture 60, 160, 160a, 260, and 360 of the main body 2 of the implant 1, 101, 101a, 201, and 301, respectively. Thus, the integration plate vertical aperture 61, 161, 161a, 261, and 361 and the body vertical aperture 60, 160, 160a, 260, and 360 preferably comprise substantially the same shape.

The integration plate 82, 182, 182a, 282, and 382 may be attached or affixed to the main body of the implant 1, 101, 101a, 201, and 301 using any suitable mechanisms known in the art. For example, the bottom surface 83, 183, 183a, 283, and 383 of the integration plate 82, 182, 182a, 282, and 382 may comprise a reciprocal connector structure, such as a plurality of posts 84, 184, 184a, 284, and 384 that align with and insert into a corresponding connector structure such as a plurality of holes 12, 112, 112a, 212, and 312 on the top surface 10, 110, 110a, 210, and 310 and/or bottom surface 20, 120, 120a, 220, and 320 of the main body 2 of the implant 1, 101, 101a, 201, and 301, respectively, and thus facilitate the connection between the integration plate 82, 182, 182a, 282, and 382 and the main body 2 of the implant 1, 101, 101a, 201, and 301. Thus, integration plates 82, 182, 182a, 282, and 382 with different sizes, shapes, or features may be used in connection with the implant 1, 101, 101a, 201, and 301, for example, to accommodate attributes of the spine of the patient into which the implant 1, 101, 101a, 201, and 301 is to be implanted. Among these different sizes, shapes, and features are lordotic angles; anti-expulsion edges 8, 108, 108a, 208, and 308; and anti-expulsion angles as described throughout this specification.

The implant 1, 101, 101a, 201, and 301 is configured to receive the integration plate 82, 182, 182a, 282, and 382, respectively. Thus, for example, the top surface 10, 110, 110a, 210, and 310 and/or bottom surface 20, 120, 120a, 220, and 320 of the implant 1, 101, 101a, 201, and 301 may be optionally recessed, and comprise a plurality of holes 12, 112, 112a, 212, and 312 that mate with the plurality of posts 84, 184, 184a, 284, and 384 on the bottom surface 83, 183, 183a, 283, and 383 of the integration plate 82, 182, 182a, 282, and 382. Thus, the plurality of posts 84, 184, 184a, 284, and 384 are inserted into the plurality of holes 12, 112, 112a, 212, and 312.

Figure 10:
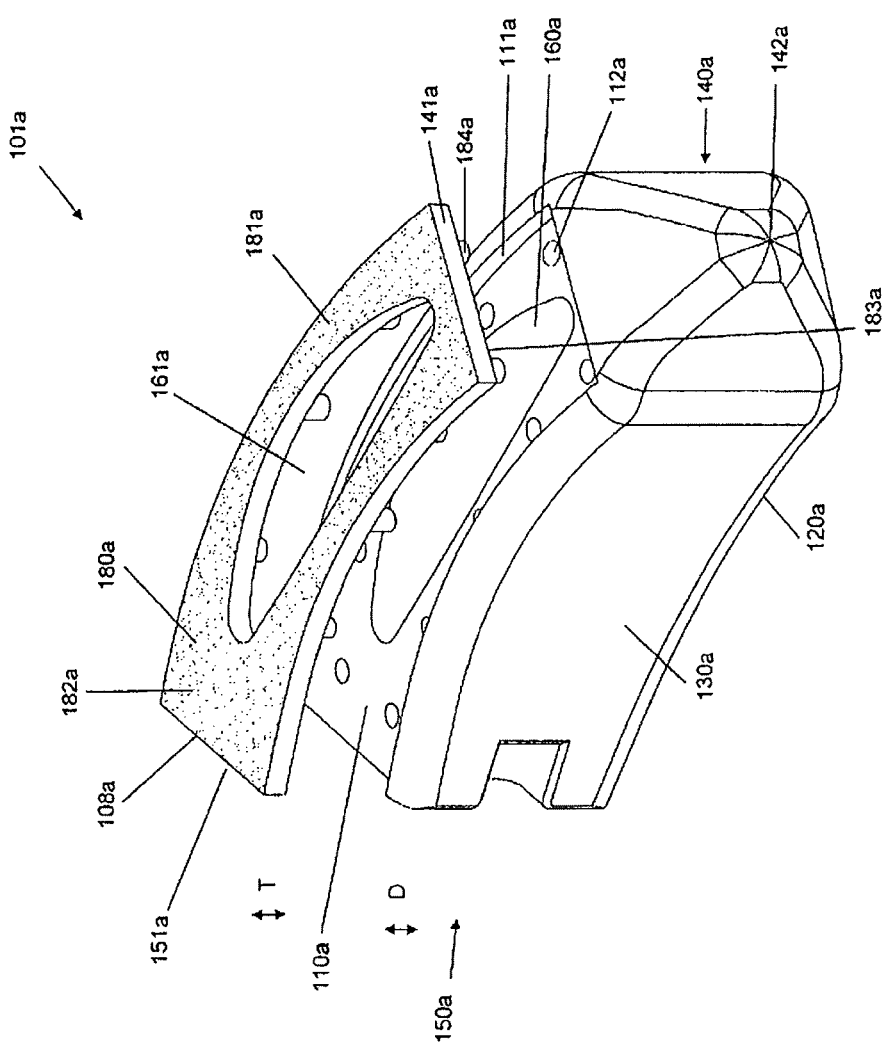
FIG. 10 shows an exploded view of a curved implant with an integration plate.
Figure 11:
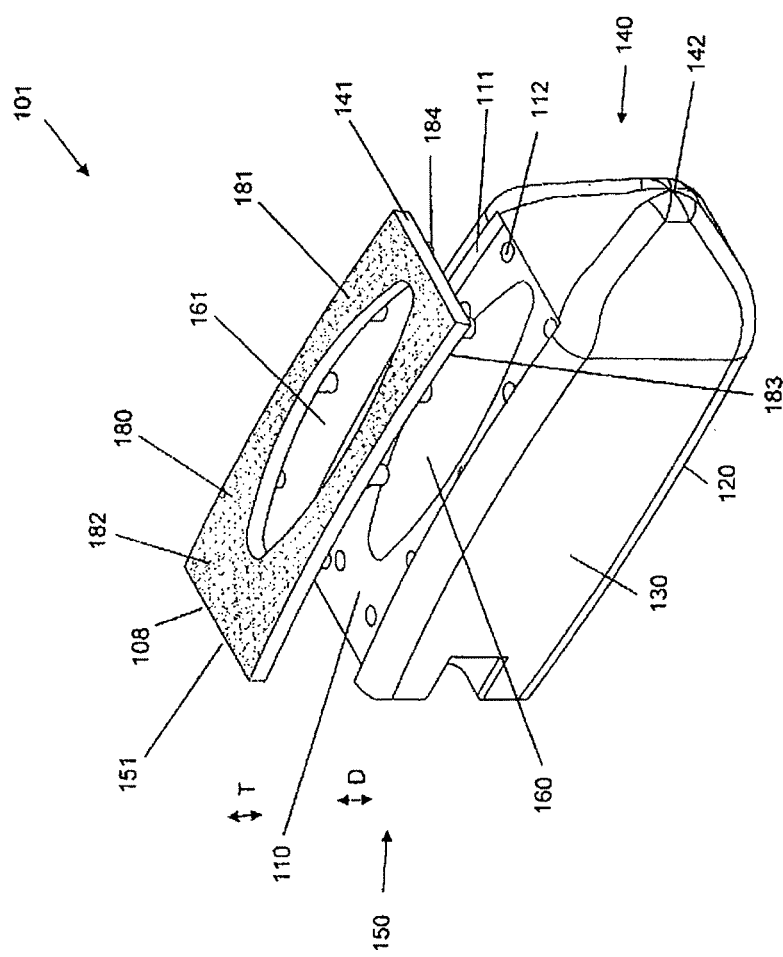
FIG. 11 shows an exploded view of a posterior implant with an integration plate.
Figure 12:
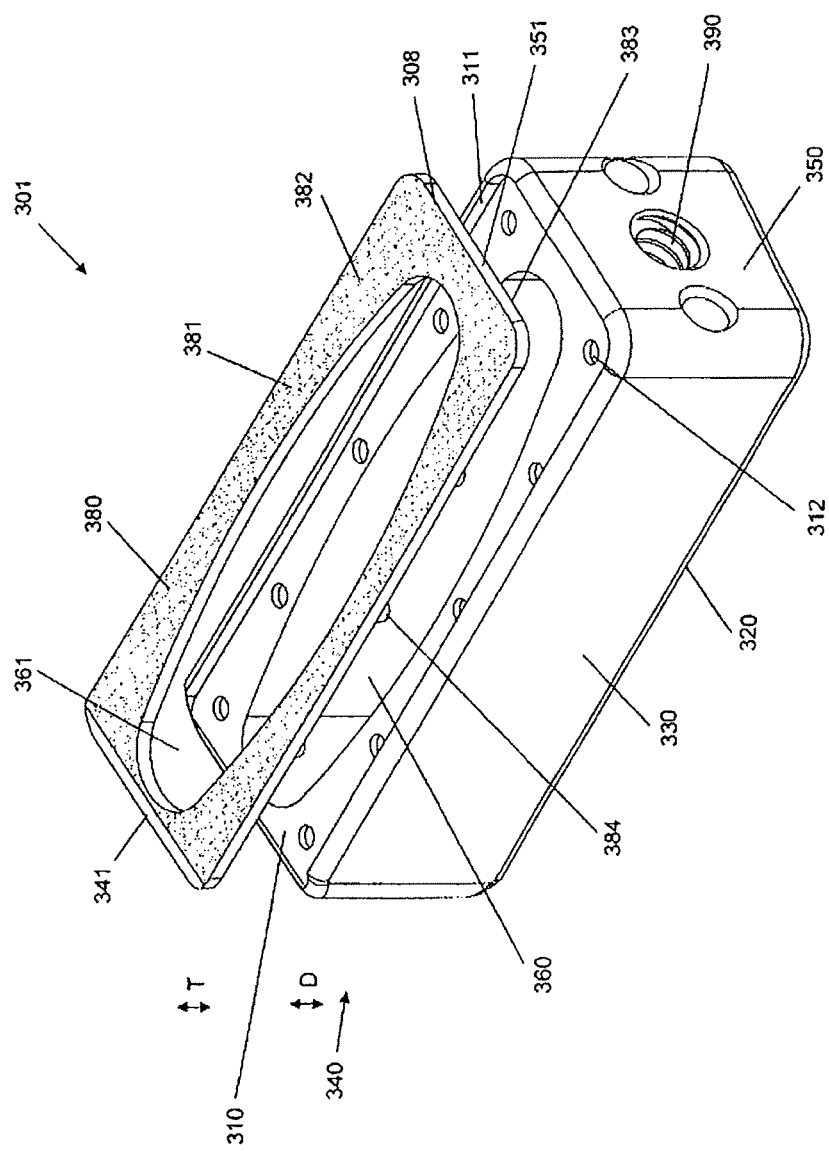
FIG. 12 shows an exploded view of a lateral lumbar implant with an integration plate.
Figure 13:
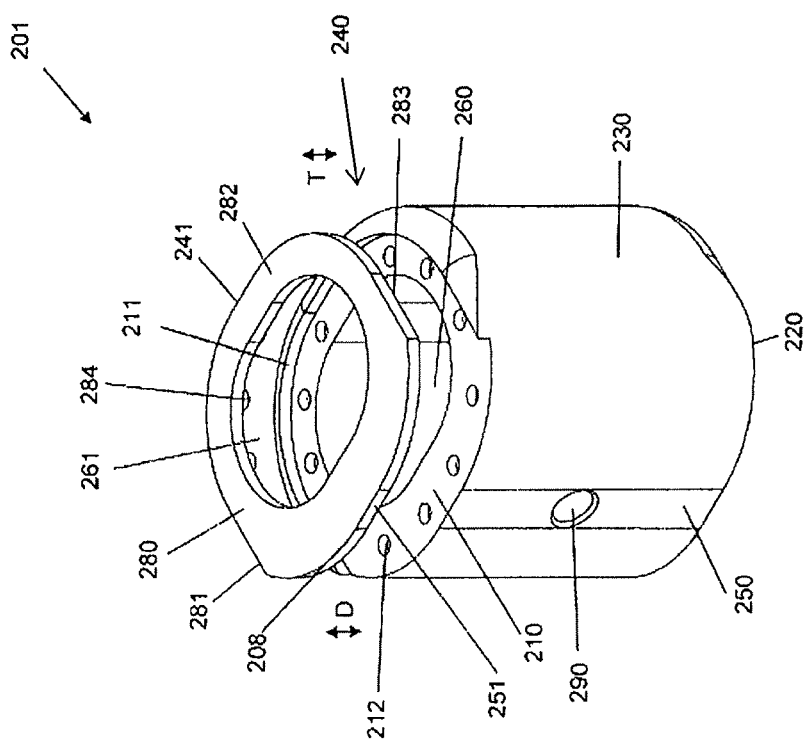
FIG. 13 shows an exploded view of a generally oval-shaped anterior cervical implant with an integration plate.

FIG. 8 shows that the top surface 10 is recessed and comprises a plurality of holes 12, but the recessed bottom surface 20 and its holes 12 are not shown. FIG. 10 shows that the top surface 110a is recessed and comprises a plurality of holes 112a, but the recessed bottom surface 120a and its holes 112a are not shown. FIG. 11 shows that the top surface 110 is recessed and comprises a plurality of holes 112, but the recessed bottom surface 120 and its holes 112 are not shown. FIG. 12 shows that the top surface 310 is recessed and comprises a plurality of holes 312, but the recessed bottom surface 320 and its holes 312 are not shown. FIG. 13 shows that the top surface 210 is recessed and comprises a plurality of holes 212, but the recessed bottom surface 220 and its holes 212 are not shown. The recess may be at a depth D, and the recess depth D preferably is uniform throughout the top surface 10, 110, 110a, 210, and 310 and/or bottom surface 20, 120, 120a, 220, and 320.

The recess depth D preferably corresponds to a thickness T of the integration plate 82, 182, 182a, 282, and 382. Thus, in some aspects, the depth D and thickness T are the same so that once the integration plate 82, 182, 182a, 282, and 382 and body of the implant 1, 101, 101a, 201, and 301, respectively, are placed together, the top surface 10, 110, 110a, 210, and 310 and/or bottom surface 20, 120, 120a, 220, and 320 of the implant 1, 101, 101a, 201, and 301 is substantially even, at least at the seam/junction between the integration plate 82, 182, 182a, 282, and 382 and the top surface 10, 110, 110a, 210, and 310 or bottom surface 20, 210, 120a, 220, and 320. In some embodiments, the posterior portion 51, 151, 151a, 251, and 351 and the anterior portion 41, 141, 141a, 241, and 341 of the integration plate 82, 182, 182a, 282, and 382 have different thicknesses such that the anterior portion 41, 141, 141a, 241, and 341 has a greater thickness than the thickness of the posterior portion 51, 151, 151a, 251, and 351.

The recess depth D and the thickness T may each independently be from about 0.1 mm to about 10 mm. In preferred aspects, the recess depth D and the thickness T may each independently be from about 1 mm to about 5 mm. Thus, for example, the recess depth D or the thickness T may be selected from about 0.1 mm, about 0.25 mm, about 0.5 mm, about 0.75 mm, about 1 mm, about 1.25 mm, about 1.5 mm, about 1.75 mm, about 2 mm, about 2.25 mm, about 2.5 mm, about 2.75 mm, about 3 mm, about 3.25 mm, about 3.5 mm, about 3.75 mm, about 4 mm, about 4.25 mm, about 4.5 mm, about 4.75 mm, about 5 mm, 5.5 mm, about 6 mm, about 6.5 mm, about 7 mm, about 75 mm, or about 8 mm.

Recessing the top surface 10, 110, 110a, 210, and 310 or bottom surface 20, 120, 120a, 220, and 320 exposes a ridge 11, 111, 111a, 211, and 311 against which the anterior portion 41, 141, 141a, 241, and 341; posterior portion 51, 151, 151a, 251, and 251; or lateral side of the integration plate 82, 182, 182a, 282, and 382 may be seated when brought together with the implant 1, 101, 101a, 201, and 301.

The integration plate 82, 182, 182a, 282, and 382 may be used with an implant suitable for ALIF (e.g., implant 1, integration plate 82), PLIF (e.g., implant 101, integration plate 182), or TLIF fusion (e.g., implant 101a, integration plate 182a); may be used with an implant suitable for cervical fusion (e.g., implant 201, integration plate 282); and may be used with an implant suitable for lateral lumbar insertion (e.g., implant 301, integration plate 382).

The reciprocal connector such as the post 84, 184, 184a, 284, and 384 preferably is secured within the connector of the body such as the hole 12, 112, 112a, 212, and 312 to mediate the connection between the integration plate 82, 182, 182a, 282, and 382 and the implant 1, 101, 101a, 201, and 301. The connection should be capable of withstanding significant loads and shear forces when implanted in the spine of the patient. The connection between the post 84, 184, 184a, 284, and 384 and the hole 12, 112, 112a, 212, and 312 may comprise a friction fit. In some aspects, the reciprocal connector such as the post 84, 184, 184a, 284, and 384 and the connector of the body such as the hole 12, 112, 112a, 212, and 312 have additional compatible structures and features to further strengthen the connection between the integration plate 82, 182, 182a, 282, and 382 and the implant 1, 101, 101a, 201, and 301.

The structures and features may be on either or both of the integration plate 82, 182, 182a, 282, and 382 and the main body 2 of the implant 1, 101, 101a, 201, and 301. In general, the structures include fasteners, compatibly shaped joints, compatibly shaped undercuts, and/or other suitable connectors having different shapes, sizes, and configurations. For example, a fastener may include a pin, screw, bolt, rod, anchor, snap, clasp, clip, clamp, or rivet. In some aspects, an adhesive may be used to further strengthen any of the integration plate 82, 182, 182a, 282, and 382 and implant 1, 101, 101a, 201, and 301 connections described in this specification. An adhesive may comprise cement, glue, polymer, epoxy, solder, weld, or other suitable binding materials.

The integration plate 82, 182, 182a, 282, and 382 may comprise one or more reciprocal connectors (not shown), such as one or more posts, each having a bore, extending through a horizontal plane. The post may be inserted into a connector such as a hole through the implant 1, 101, 101a, 201, and 301. A fastener (not shown), such as a pin, may be inserted through the bore thereby preventing the post from being disengaged from the hole. In some aspects, the pin may be threaded through a second bore that passes through the walls of the implant 1, 101, 101a, 201, and 301 itself; although it is preferable that the implant 1, 101, 101a, 201, and 301 does not include a second bore through its walls and that the bore is accessible from the space inside of the implant. Alternatively, the integration plate 82, 182, 182a, 282, and 382 may comprise a plurality of bores (not shown) present on and having openings accessible from the bottom of the integration plate 82, 182, 182a, 282, and 382. The bores may mate with a plurality of fasteners, which may comprise rods integral with or otherwise attached to the top surface or bottom surface of the implant 1, 101, 101a, 201, and 301. For example, the rods may be molded as upward-facing extensions or snap-fit into the bores. In some aspects, for example, where the body 2 of the implant 1, 101, 101a, 201, and 301 is comprised of a plastic or polymeric material, the hole 12, 112, 112a, 212, and 312 may not be present, and the screw or bolt (not shown) may be screwed directly into the plastic or polymeric material, with the screw threads tightly gripping the plastic or polymeric material to form the connection.

It is also contemplated that the bottom surface 83, 183, 183a, 283, and 383 of the integration plate 82, 182, 182a, 282, and 382 may comprise undercuts (not shown) in shapes that form a tight junction with compatible shapes on the implant 1, 101, 101a, 201, and 301. For example, the bottom surface 83, 183, 183a, 283, and 383 may comprise a dovetail joint, bevel, or taper that fits with a counterpart dovetail joint, bevel, or taper on the body 2 of the implant 1, 101, 101a, 201, and 301.

An adhesive (not shown) may directly join the integration plate 82, 182, 182a, 282, and 382 and the body 2 of the implant 1, 101, 101a, 201, and 301 together, with or without other connecting features. For example, the adhesive may be applied to the bottom surface 83, 183, 183a, 283, and 383 of the integration plate 82, 182, 182a, 282, and 382. Alternatively, the adhesive may be applied to the top surface 10, 110, 110a, 210, and 310 or bottom surface 20, 120, 120a, 220, and 320 or both surfaces of the implant 1, 101, 101a, 201, and 301.

The foregoing describes various non-limiting examples of how the one or two integration plates 82, 182, 182*a*, 282, and 382 may be joined together with the implant 1, 101, 101*a*, 201, and 301.

The implant 1 may be machined to comprise some or all of the following implant features, for example. In some aspects, the interbody spinal implant 1 is substantially hollow and has a generally oval-shaped transverse cross-sectional area with smooth, rounded, or both smooth and rounded lateral sides 30 and posterior-lateral corners. The implant 1 includes at least one vertical aperture 60 that extends the entire height of the implant body 2. The vertical aperture 60 defines an interior surface or hollow cavity within the implant 1, which may be filled with bone growth inducing materials. The vertical aperture (a) extends from the top surface to the bottom surface, (b) has a size and shape predetermined to maximize the surface area of the top surface and the bottom surface available proximate the anterior and posterior portions while maximizing both radiographic visualization and access to the substantially hollow center, and (c) optionally defines a transverse rim. The vertical aperture 60 may further define a transverse rim 100 having a greater posterior portion thickness 55 than an anterior portion thickness 45.

In at least one embodiment, the opposing lateral sides 30 and the anterior portion 40 have a rim thickness 45 of about 5 mm, while the posterior portion 50 has a rim thickness 55 of about 7 mm. Thus, the rim posterior portion thickness 55 may allow for better stress sharing between the implant 1 and the adjacent vertebral endplates and helps to compensate for the weaker posterior endplate bone. In some aspects, the transverse rim 100 has a generally large surface area and contacts the vertebral endplate. The transverse rim 100 may act to better distribute contact stresses upon the implant 1, and hence minimize the risk of subsidence while maximizing contact with the apophyseal supportive bone. It is also possible for the transverse rim 100 to have a substantially constant thickness (e.g., for the anterior portion thickness 45 to be substantially the same as the posterior portion thickness 55) or for the posterior portion 50 to have a rim thickness 55 less than that of the opposing lateral sides 30 and the anterior portion 40.

The implant 1 may be shaped to reduce the risk of subsidence, and improve stability, by maximizing contact with the apophyseal rim of vertebral endplates. Embodiments may be provided in a variety of anatomical footprints having a medial-lateral width ranging from about 32 mm to about 44 mm. An interbody spinal implant 1 generally does not require extensive supplemental or obstructive implant instrumentation to maintain the prepared disc space during implantation. Thus, the interbody spinal implant 1 and associated implantation methods allow for larger-sized implants as compared with other size-limited interbody spinal implants known in the art. This advantage allows for greater medial-lateral width and correspondingly greater contact with the apophyseal rim.

As illustrated in FIG. 7A and FIG. 8, the implant 1 has an opening 90 in the anterior portion 40. In one embodiment, the posterior portion 50 may have a similarly shaped opening 90 (not shown). In some aspects, only the anterior portion 40 has the opening 90 while the posterior portion 50 has an alternative opening 92 (which may have a size and shape different from the opening 90). The opening 92 defines an interior surface 92*a* or hollow cavity, which may be filled with bone growth inducing materials.

The opening 90, 290, and 390 has a number of functions. One function is to facilitate manipulation of the implant 1, 201, and 301 by the caretaker. Thus, the caretaker may insert a surgical tool into the opening 90, 290, and 390 and, through the engagement between the surgical tool and the opening 90, 290, and 390, manipulate the implant 1, 201, and 301. The opening 90, 290, and 390 may be threaded to enhance the engagement. A suitable surgical tool, such as a distractor (not shown), may be selected by one of ordinary skill in the art.

As best shown in FIGS. 10 and 11, the anterior portion 140, 140*a* may have a tapered nose 142, 142*a* to facilitate insertion of the implant 101.

The implant 1 may further include at least one transverse aperture 70 that extends the entire transverse length of the implant body. The transverse aperture 70 defines an interior surface or hollow cavity, which may be filled with bone growth inducing materials. The at least one transverse aperture 70 may provide improved visibility of the implant 1 during surgical procedures to ensure proper implant placement and seating, and may also improve post-operative assessment of implant fusion. The transverse aperture 70 may be broken into two, separate sections by an intermediate wall. Suitable shapes and dimensions for the transverse aperture 70 may be selected by one of ordinary skill in the art. In particular, all edges of the transverse aperture 70 may be rounded, smooth, or both. The intermediate wall may be made of the same material as the remainder of the body 2 of the implant 1 (e.g., plastic), or it may be made of another material (e.g., metal). The intermediate wall may offer one or more of several advantages, including reinforcement of the implant 1 and improved bone graft containment.

The implant 1 may be provided with a solid rear wall (not shown). The rear wall may extend the entire width of the implant body and nearly the entire height of the implant body. Thus, the rear wall can essentially close the anterior portion 40 of the implant 1. The rear wall may offer one or more of several advantages, including reinforcement of the implant 1 and improved bone graft containment. In the cervical application, it may be important to prevent bone graft material from entering the spinal canal.

The implant 1 may also have a lordotic angle to facilitate alignment. The anterior portion 40 is preferably generally greater in height than the opposing posterior portion 50. Therefore, the implant 1 may better compensate for the generally less supportive bone found in certain regions of the vertebral endplate. As much as seven degrees of lordosis (or more) may be built into the implant 1 to help restore cervical balance.

To enhance movement resistance and provide additional stability under spinal loads in the body, the implant 1, 101, 101*a*, 201, and 301 may comprise one or more anti-expulsion edges 8, 108, 108*a*, 208, and 308 that tend to "dig" into the end-plates slightly and help to resist expulsion. The anti-expulsion edges 8, 108, 108*a*, 208, and 308 may be present on the top surface 81 of the integration plate 82 affixed to the top surface 10, 110, 110*a*, 210, and 310; the bottom surface 20, 120, 120*a*, 220, and 320; or both surfaces of the implant 1, 101, 101*a*, 201, and 301. Alternatively, the anti-expulsion edges 8, 108, 108*a*, 208, and 308 may be present on the top surface 10, 110, 110*a*, 210, and 310; the bottom surface 20, 120, 120*a*, 220, and 320; or both surfaces of the body 2 of the implant 1, 101, 101*a*, 201, and 301. The anti-expulsion edges 8, 108, 108*a*, 208, and 308 may be formed, for example, when the edge of the blank 6 is cut or trimmed (e.g., a trimmed edge). The edge of the blank 6 which ultimately forms the anti-expulsion edges 8, 108, 108*a*, 208, and 308 may be cut before, during, or after the roughened surface topography is applied to a surface of blank 6 via the subtractive process described above.

By way of example, FIG. 8 shows an anti-expulsion edge 8 on the top surface 81 of the integration plate 82 and the bottom surface 20 of the anterior face 40 of the implant 1. Each anti-expulsion edge 8 may protrude above the plane of the top surface 81 of the integration plate 82 and bottom surface 20, with the amount of protrusion increasing toward the anterior face 40 and the highest protrusion height P at the anterior-most edge of the top surface 81 of the integration plate 82 or bottom surface 20.

An anti-expulsion edge 8, 108, 108*a*, 208, and 308 may be oriented toward the anterior portion 40, 140, 140*a*, 240, and 340, or the posterior portion 50, 150, 150*a*, 250, and 350, or either of the opposing lateral sides 30, 130, 130*a*, 230, and 330. The orientation of the anti-expulsion edge 8, 108, 108*a*, 208, and 308 may depend on the intended orientation of the implant 1, 101, 101*a*, 201, and 301 when it has been implanted between vertebrae in the patient.

EXAMPLE SURGICAL METHODS

The following examples of surgical methods are included to more clearly demonstrate the overall nature of the invention. These examples are exemplary, not restrictive, of the invention.

Certain embodiments of the invention are particularly suited for use during interbody spinal implant procedures currently known in the art. For example, the disc space may be accessed using a standard mini open retroperitoneal laparotomy approach. The center of the disc space is located by AP fluoroscopy taking care to make sure the pedicles are equidistant from the spinous process. The disc space is then incised by making a window in the annulus for insertion of certain embodiments of the spinal implant 1, 101, 101*a*, 201, and 301 (a 32 or 36 mm window in the annulus is typically suitable for insertion). The process according to the invention minimizes, if it does not eliminate, the cutting of bone. The endplates are cleaned of all cartilage with a curette, however, and a size-specific rasp (or broach) may then be used.

Use of a rasp preferably substantially minimizes or eliminates removal of bone, thus substantially minimizing or eliminating impact to the natural anatomical arch, or concavity, of the vertebral endplate while preserving much of the apophyseal rim. Preservation of the anatomical concavity is particularly advantageous in maintaining biomechanical integrity of the spine. For example, in a healthy spine, the transfer of compressive loads from the vertebrae to the spinal disc is achieved via hoop stresses acting upon the natural arch of the endplate. The distribution of forces, and resultant hoop stress, along the natural arch allows the relatively thin shell of subchondral bone to transfer large amounts of load.

During traditional fusion procedures, the vertebral endplate natural arch may be significantly removed due to excessive surface preparation for implant placement and seating. This is especially common where the implant 1, 101, 101*a*, 201, and 301 is to be seated near the center of the vertebral endplate or the implant 1, 101, 101*a*, 201, and 301 is of relatively small medial-lateral width. Breaching the vertebral endplate natural arch disrupts the biomechanical integrity of the vertebral endplate such that shear stress, rather than hoop stress, acts upon the endplate surface. This redistribution of stresses may result in subsidence of the implant 1, 101, 101*a*, 201, and 301 into the vertebral body.

Preferred embodiments of the surgical method minimize endplate bone removal on the whole, while still allowing for some removal along the vertebral endplate far lateral edges where the subchondral bone is thickest. Still further, certain embodiments of the interbody spinal implant 1, 101, 101*a*, 201, and 301 include smooth, rounded, and highly radiused posterior portions and lateral sides which may minimize extraneous bone removal for endplate preparation and reduce localized stress concentrations. Thus, interbody surgical implant 1, 101, 101*a*, 201, and 301 and methods of using it are particularly useful in preserving the natural arch of the vertebral endplate and minimizing the chance of implant subsidence.

Because the endplates are spared during the process of inserting the spinal implant 1, 101, 101*a*, 201, and 301, hoop stress of the inferior and superior endplates is maintained. Spared endplates allow the transfer of axial stress to the apophasis. Endplate flexion allows the bone graft placed in the interior of the spinal implant 1, 101, 101*a*, 201, and 301 to accept and share stress transmitted from the endplates. In addition, spared endplates minimize the concern that BMP might erode the cancellous bone.

Interbody spinal implant 1, 101, 101*a*, 201, and 301 is durable and can be impacted between the endplates with standard instrumentation. Therefore, certain embodiments of the invention may be used as the final distractor during implantation. In this manner, the disc space may be under-distracted (e.g., distracted to some height less than the height of the interbody spinal implant 1) to facilitate press-fit implantation. Further, certain embodiments of the current invention having a smooth and rounded posterior portion (and lateral sides) may facilitate easier insertion into the disc space. Still further, the surface roughened topography 80 may lessen the risk of excessive bone removal during distraction as compared to implants having teeth, ridges, or threads currently known in the art even in view of a press-fit surgical distraction method. Nonetheless, once implanted, the interbody surgical implant 1, 101, 101*a*, 201, and 301 may provide secure seating and prove difficult to remove. Thus, certain embodiments of the interbody spinal implant 1, 101, 101*a*, 201, and 301 may maintain a position between the vertebral endplates due, at least in part, to resultant annular tension attributable to press-fit surgical implantation and, post-operatively, improved osteointegration.

Surgical implants and methods according to embodiments of the invention tension the vertebral annulus via distraction. These embodiments may also restore spinal lordosis, thus improving sagittal and coronal alignment. Implant systems currently known in the art require additional instrumentation, such as distraction plugs, to tension the annulus. These distraction plugs require further tertiary instrumentation, however, to maintain the lordotic correction during actual spinal implant insertion. If tertiary instrumentation is not used, then some amount of lordotic correction may be lost upon distraction plug removal. Interbody spinal implant 1, 101, 101*a*, 201, and 301, according to certain embodiments of the invention, is particularly advantageous in improving spinal lordosis without the need for tertiary instrumentation, thus reducing the instrument load upon the surgeon. This reduced instrument load may further decrease the complexity, and required steps, of the implantation procedure.

Certain embodiments of the spinal implant 1, 101, 101*a*, 201, and 301 may also reduce deformities (such as isthmic spondylolythesis) caused by distraction implant methods. Traditional implant systems require secondary or additional instrumentation to maintain the relative position of the vertebrae or distract collapsed disc spaces. In contrast, interbody spinal implant 1, 101, 101a, 201, and 301 may be used as the final distractor and thus maintain the relative position of the vertebrae without the need for secondary instrumentation.

Certain embodiments collectively comprise a family of implants, each having a common design philosophy. These implants 1, 101, 101a, 201, and 301 and the associated surgical technique have been designed to address at least the ten, separate challenges associated with the current generation of traditional anterior spinal fusion devices listed above in the Background section of this document.

After desired annulotomy and discectomy, embodiments of the invention first adequately distract the disc space by inserting (through impaction) and removing sequentially larger sizes of very smooth distractors, which have been size matched with the size of the available implant 1, 101, 101a, 201, and 301. Once adequate distraction is achieved, the surgeon prepares the end-plate with a rasp. There is no secondary instrumentation required to keep the disc space distracted while the implant 1, 101, 101a, 201, and 301 is inserted, as the implant 1, 101, 101a, 201, and 301 has sufficient mechanical strength that it is impacted into the disc space. In fact, the height of the implant 1, 101, 101a, 201, and 301 is preferably about 1 mm greater than the height of the rasp used for end-plate preparation, to create some additional tension in the annulus by implantation, which creates a stable implant construct in the disc space.

The implant geometry has features which allow it to be implanted via any one of an anterior, antero-lateral, or lateral approach, providing tremendous intra-operative flexibility of options. The implant 1, 101, 101a, 201, and 301 has adequate strength to allow impact, and the sides of the implant 1, 101, 101a, 201, and 301 may have smooth surfaces to allow for easy implantation and, specifically, to prevent binding of the implant 1, 101, 101a, 201, and 301 to soft tissues during implantation.

The invention encompasses a number of different implant 1, 101, 101a, 201, and 301 configurations, including a composite implant 1, 101, 101a, 201, and 301 formed of top and optional bottom plates (components), for example, made out of titanium. The integration surfaces exposed to the vertebral body have a roughened surface topography 80 to allow for bony in-growth over time, and to provide resistance against expulsion. The top and bottom titanium plates may be assembled together with the implant body 2. The net result is a composite implant 1, 101, 101a, 201, and 301 that has engineered stiffness for its clinical application. The axial load may be borne by the polymeric component of the construct.

It is believed that an intact vertebral end-plate deflects like a diaphragm under axial compressive loads generated due to physiologic activities. If a spinal fusion implant 1, 101, 101a, 201, and 301 is inserted in the prepared disc space via a procedure which does not destroy the end-plates, and if the implant 1, 101, 101a, 201, and 301 contacts the end-plates only peripherally, the central dome of the end-plates can still deflect under physiologic loads. This deflection of the dome can pressurize the bone graft material packed inside the spinal implant, hence allowing it to heal naturally. The implant 1, 101, 101a, 201, and 301 designed according to certain embodiments allows the vertebral end-plate to deflect and allows healing of the bone graft into fusion.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

What is claimed is:

1. A method of producing an interbody spinal implant, comprising
applying a subtractive process to at least one surface of a metal blank to form a roughened surface topography on the at least one surface, the surface topography comprising micro features having a maximum peak to valley height within the micrometer size scale and nano features having a maximum peak to valley height within the nanometer size scale; and
subsequently, machining the blank to form an interbody spinal implant including a body having a shape for implantation into an intervertebral disc space through the posterior, the anterior, a lateral side, or the foramen of the spine, having surface structures that preserve vertebral endplate bone, that provide stability of the implant in the intervertebral disc space, and that resist expulsion of the implant from the intervertebral disc space, and having at least one vertical aperture for graft containment.

2. The method of claim 1 further comprising applying a maskant to the blank before applying the subtractive process.

3. The method of claim 2, wherein the maskant is applied via sputtering, deposition, or evaporation.

4. The method of claim 1, wherein the roughened surface topography is oriented in opposition to the biologic forces on the interbody spinal implant and to the direction of implantation.

5. The method of claim 1, wherein the roughened surface topography promotes bone growth.

6. The method of claim 1, wherein the roughened surface topography further comprises a roughness average amplitude, Ra, of about 1 to 200 microns.

7. The method of claim 1, where the subtractive process comprises abrasive blasting of the at least one surface.

8. The method of claim 7, wherein the subtractive process further comprises chemical etching the at least one surface.

9. The method of claim 8, wherein the chemical etching comprises mild acid etching.

10. The method of claim 1, wherein the subtractive process comprises chemical etching of the at least one surface.

11. The method of claim 1, wherein the machining includes milling, turning, or both milling and turning.

12. The method of claim 1, further comprising machining the body to include a slope or angle.

13. The method of claim 1, wherein the metal comprises titanium or a titanium alloy.

14. The method of claim 1, further comprising machining the body to include smooth, rounded, or smooth and rounded sides or corners.

* * * * *